United States Patent [19]
Hjertman et al.

[11] Patent Number: 6,042,571
[45] Date of Patent: Mar. 28, 2000

[54] INJECTION DEVICE

[75] Inventors: Birger Hjertman, Vällingby; Rudolf Cseke, Sollentuna; Gunnar Pettersson, Åkersberga, all of Sweden; Guido Hertig, Fraubrunnen; Rainer Bosse, Kirchberg, both of Switzerland

[73] Assignee: Pharmacia & Upjohn Aktiebolag, Stockholm, Sweden

[21] Appl. No.: 08/886,515

[22] Filed: Jul. 1, 1997

Related U.S. Application Data

[60] Provisional application No. 60/021,293, Jul. 9, 1996.

[30] Foreign Application Priority Data

Jul. 1, 1996 [SE] Sweden .................. 9602611

[51] Int. Cl.⁷ ................................. A61M 5/24
[52] U.S. Cl. .................... 604/208; 604/211; 604/228
[58] Field of Search .................... 604/131, 151, 604/154, 155, 207, 208, 211, 232, 234, 218, 224, 228

[56] References Cited

U.S. PATENT DOCUMENTS

| | | | |
|---|---|---|---|
| 4,529,401 | 7/1985 | Leslie et al. | 604/131 |
| 4,585,439 | 4/1986 | Michel | 604/155 |
| 4,833,384 | 5/1989 | Munro et al. | 318/687 |
| 4,874,381 | 10/1989 | Vetter | 604/191 |
| 4,950,246 | 8/1990 | Muller | 604/154 |
| 4,968,299 | 11/1990 | Ahlstrand et al. | 604/90 |
| 5,106,375 | 4/1992 | Conero | 604/155 |
| 5,112,317 | 5/1992 | Michel | 604/208 |
| 5,139,484 | 8/1992 | Hazon et al. | 604/154 |
| 5,232,459 | 8/1993 | Hjertman | 604/208 |
| 5,360,410 | 11/1994 | Wacks | 604/232 |
| 5,435,076 | 7/1995 | Hjertman et al. | 34/296 |
| 5,501,673 | 3/1996 | Hjertman et al. | 604/191 |
| 5,536,249 | 7/1996 | Castellano et al. | 604/65 |
| 5,593,390 | 1/1997 | Castellano et al. | 604/187 |

FOREIGN PATENT DOCUMENTS

| | | | |
|---|---|---|---|
| 0 092 712 A2 | 11/1983 | European Pat. Off. | A61M 5/14 |
| 27 10 433 | 9/1977 | Germany | A61M 5/20 |
| WO 96/05878 | 2/1996 | Japan | A61M 5/31 |
| 9503685 | of 1995 | Sweden . | |
| WO 85/02546 | 6/1985 | WIPO | A61M 5/14 |
| WO 95/11051 | of 1995 | WIPO . | |

*Primary Examiner*—Corrine McDermott
*Attorney, Agent, or Firm*—Pollock, Vande Sande & Amernick

[57] ABSTRACT

An injection device comprising a) a housing, b) a cartridge containing a preparation or precursor components for the preparation and having a front part and a rear part defining a general cartridge axis, an outlet for the preparation arranged at the front part and at least one movable wall arranged between the front part and the rear part, a displacement of which wall causes the preparation to be moved towards or expelled through the outlet, c) a piston rod, having a first end and a second end, at least partly contained within the housing and being operable to engage and displace the movable wall at its first end and d) actuating means within the housing arranged to move at least the rod. According to the invention the device comprises gripping means connected to the housing and arranged to hold the cartridge, or an enclosure therefore, with its front part distal and its rear part proximal to the housing, the actuating means being arranged to move the gripping means so as to move the cartridge, with its rear part leading, relative the housing, locking means able to lock the cartridge against axial movements relative to the housing, hereby defining a locked position for the cartridge, the actuating means being able to move the piston rod between at least one retracted position and at least one extended position, and the relative positions between the piston rod in its retracted position and the cartridge in its locked position being such that the piston rod extends into the cartridge. The invention also relates to a method for operating the device.

43 Claims, 8 Drawing Sheets

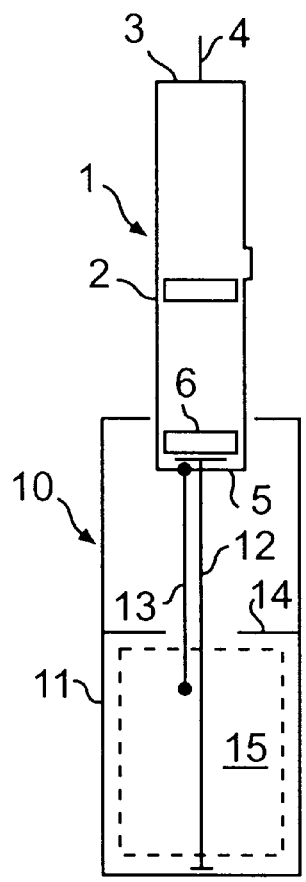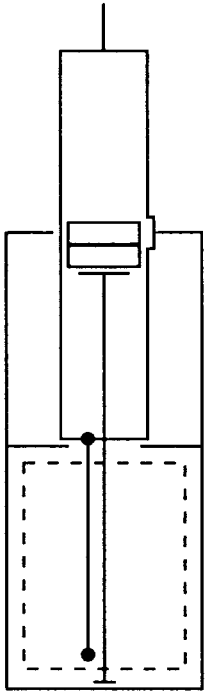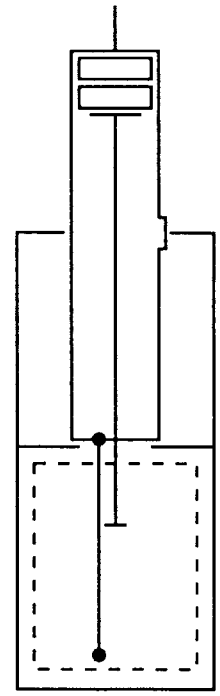
FIG. 1A  FIG. 1B  FIG. 1C
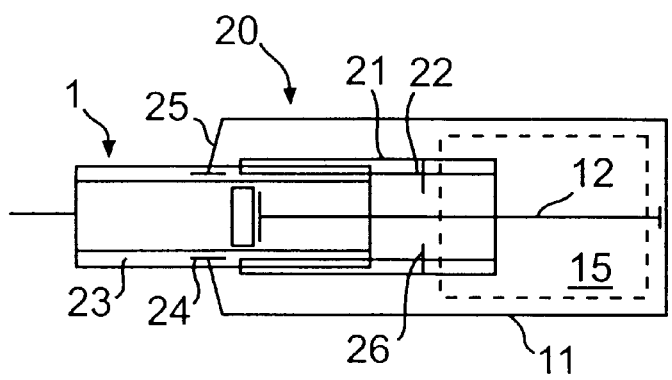
FIG. 2

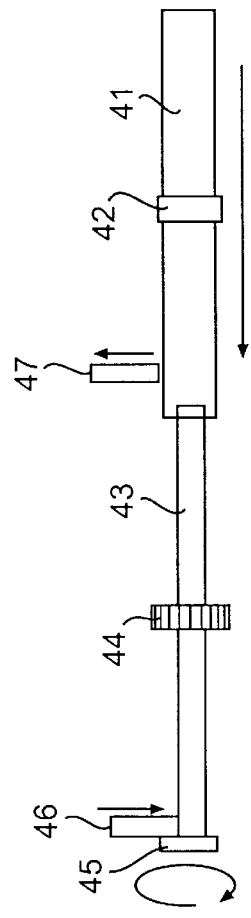
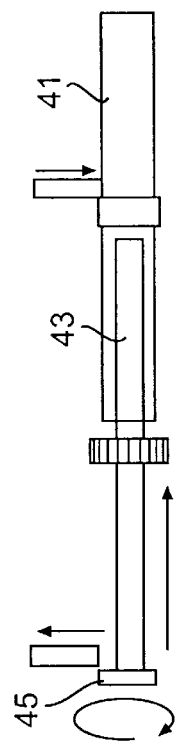
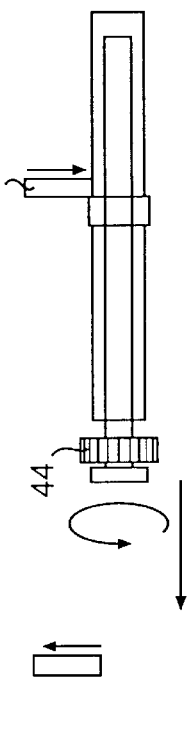
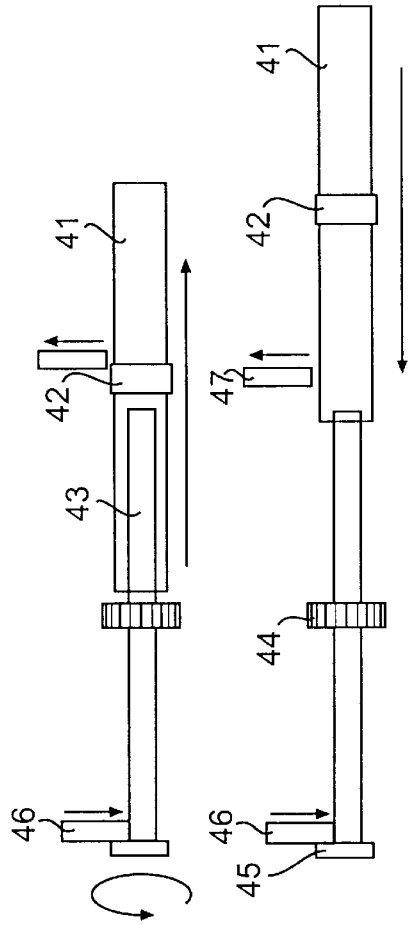
FIG. 4A  FIG. 4B  FIG. 4C  FIG. 4D  FIG. 4E

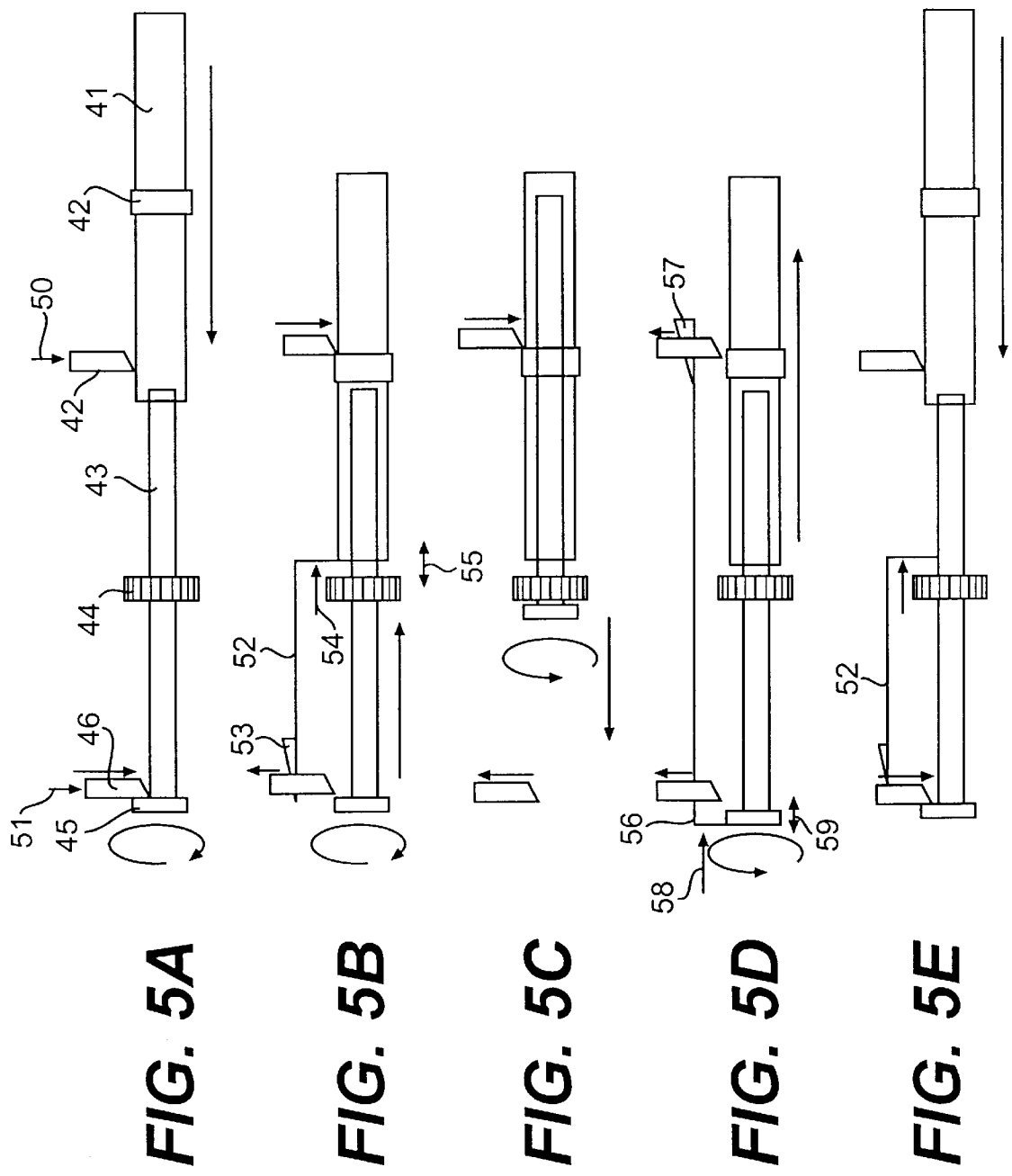

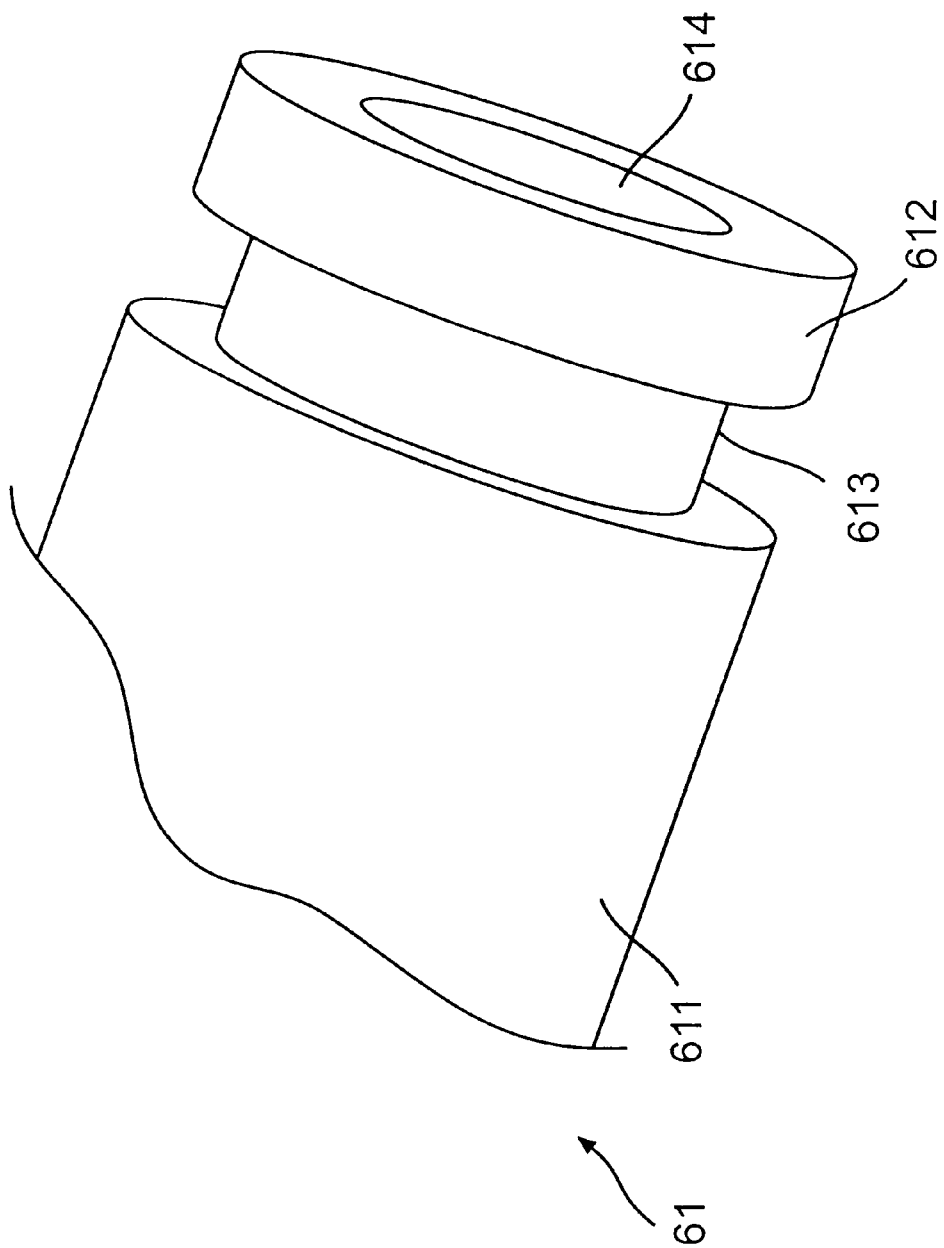

INJECTION DEVICE

This application claims the benefit of U.S. Provisional Application Ser. No. 60/021,293 filed Jul. 9, 1996.

TECHNICAL FIELD

The present invention relates to an injection device and a method for its operation, wherein the injection device is of the type comprising a) a housing, b) a cartridge containing a preparation or precursor components for the preparation and having a front part and a rear part defining a general cartridge axis, an outlet for the preparation arranged at the front part and at least one movable wall arranged between the front part and the rear part, a displacement of which wall causes the preparation to be moved towards or expelled through the outlet c) a rod at least partly contained within the housing and being operable to engage and displace the movable wall and d) actuating means within the housing arranged to move at least the rod.

BACKGROUND OF THE INVENTION

Injection devices based on a separate housing and replaceable cartridges have found widespread use in many areas, such as medical delivery systems, owing to the flexibility and economy contained in the possibility of providing the reusable housing with more or less advanced machinery for preparing, dosing, controlling and monitoring the injection procedure whereas the replaceable cartridge features can be limited to those necessary for safe confinement and simple expulsion of the pharmaceutical, features which furthermore may be adapted to each individual preparation type.

In more permanent set-ups, e.g. for hospital treatment situations, there are few design restrictions and the housing part can be highly sophisticated in view of motorized manipulation means, processor controlled operation and data collection as well as possible interfacing against other available instrumentation. Often the design freedom is also utilized to make the housing part compatible with one or several existing or standardized cartridge, syringe or injection device types, hereby increasing the application range for the instrument and reducing adaptation costs for the cartridge part.

For ambulatory purposes the design limitations are more severe, especially for self-contained devices without connectable support. Size and weight restrictions place limitations on the number and sophistication degree of functions possible to include. Automation as an alternative measure for increasing safety and avoiding misuse is similarly restricted by the added motorized means and operation repertoire by limited capacity of energy storage means.

Yet the devices have to meet all regular safety and precision aspects not only in the dosing step itself, which should allow for both multiple injections of equal and unchanged amounts as well as of precisely set individual doses, but also correct sequence and performance of initiating steps, such as mixing, deaeration and pre-ejection. The problems become more pronounced with pharmaceuticals having a limited storage stability requiring preparation steps immediately before use or being shear-sensitive and requiring preparation and dosing under controlled mechanical conditions. Two or multiple chamber cartridges are frequently used for medical requiring a reconstitution step, such as the dissolution of a stable lyophilized powder in one chamber with a solvent in another chamber. Besides the additional preparation step the multiple chamber cartridges pose special problems to size reduction efforts since they are typically larger than single chamber cartridges, partly because of necessary mixing space and partly because of the additional walls and mixing structures.

Although handy and portable injectors may be devised with the minimum of support features necessary to safely control all the abovesaid requirements and problems in the hands of a skilled operator, a general trend in long-term medication is to place the administration responsibility on the patient himself, also in the case of child or disabled persons, e.g. by use of pen-type injectors. A high degree of automation and control is then desirable to avoid mistakes, not only at the mere injections steps but also the critical initiation and preparation steps. Patients dependent on daily administrations also have a legitimate need for convenience and devices discrete enough to be brought around in daily life. The contradictory requirements on highly sophisticated and yet small and convenient devices are not met by known prior art suggestions.

The U.S. Pat. Nos. 5,112,317 and 5,232,459 describes typical mechanical and manually operated portable multi-dose devices in which size is minimized by allowing the devices to shrink in accord with medical consumption, in the first reference by a linear and in the second reference by a threaded retraction of an ampoule containing part into the device main part. In order not to cause problem during injection the dosing mechanism must necessarily operate in an intermittent manner unsuitable for further automation and in itself size an resource demanding. No special features are present to facilitate and secure preparatory or initiating steps before dosing.

The patent specifications U.S. Pat. No. 4,874,381, U.S. Pat. No. 4,968,299 and WO 96/05878 describe similar manually operated devices which provides for an initiation step in which medical reconstitution takes place in a two compartment cartridge. In order to safeguard a slow and cautious internal liquid transfer the relative motion between piston rod and cartridge is performed between threaded parts. Besides having the abovementioned general limitations to further automation, nothing facilitates safe shift of control between the reconstitution step and the dosing steps.

Injection devices with motorized and automation means are disclosed in several prior patent specifications as represented by e.g. U.S. Pat. No. 4,529,401, U.S. Pat. No. 4,833,384, U.S. Pat. No. 5,106,375, U.S. 5,139,484, EP 143,895, EP 293,958, DE 2,710,433. WO 85/02546 and WO 95/24233. Generally these devices are either only suited in permanent installations or, when suggested for mobile use, are ungainly with low cartridge to overall size ratio. They all lack cartridge preparation features with corresponding control means. The WO 93/02720 reference discloses a two compartment type cartridge system that may be used in a portable device. Aside from a special needle retraction system the reconstitution principle is entirely conventional without any utilization of automation possibilities Accordingly there is a continuing need for portable injection devices relieving patients under self-administration from the burden of learning and controlling in a fail-safe manner every step in the administration scheme, preferably by building a high degree of automation into the devices, while still satisfying the patients legitimate desire for easy to use and discrete design. Although the present invention has a more general utility, it will mainly be described against this background.

SUMMARY OF THE INVENTION

A main object of the present invention is to avoid or ameliorate the abovesaid disadvantages of known devices. A more specific object is to offer a convenient and moderately sized device and operation method suitable for ambulatory use. A further object is to offer a device facilitating operation and reducing risks for and hazards in possible misuse. Still another object is to offer a device suitable for automation and motorized operation. Yet another object is to provide such a device with improved possibilities for self-control. A further object is to provide a device facilitating initiation. Another object is to provide such a device suitable for multi-chamber cartridges and simplifying reconstitution steps in connection therewith.

These objects are reached with the characteristics and improvements set forth in the appended claims.

According to one aspect of the invention a device of the initially stated type has gripping means arranged to grip and hold the cartridge and actuating means for moving the cartridge relative the housing to a locked position in which the piston rod extends into the cartridge. According to an operating method the corresponding movement up to locking displaces the cartridge movable wall at least partially after which the main dosing expulsions can be performed. Gripping and moving the cartridge relative the housing in the claimed manner allow for controlled insertion of the cartridge in the device. The presence of the piston rod within the cartridge after this step in itself acts to lock the cartridge against lateral movements to thereby prevent unintended and dangerous interprocedural removal, which safety measure can be further elaborated on by additional locking means. Movement under displacement of the movable cartridge wall permits simple and controlled initiation of the injection device. Normally such initiation is a coherent step procedure, clearly distinguished from the subsequent main operation of performing injection. By moving the cartridge during this step final device size will exclude the length required for the initiation and in principle the stroke length of a piston rod can be limited to what is needed for expulsion of final preparation. The same features make it possible to employ and benefit from small cartridge types. Axial locking allows for shift of control from initiation to injection and stable device size during the latter steps. The abovesaid general advantages are amplified when combined with automation means. Gripping and moving with actuating means permit controlled and adapted initiation in a fail-safe manner also for highly sensitive preparations. The movement as such facilitates automatic sensing of cartridge characteristics, such as condition, content or any identity code provided, by the scanning action from even a stationary probe or sensor. Size conservation and possibility of using shorter piston rods allows for additional functions without undue bulkiness. A shift of control from initiation to injection is facilitated by the clear two-step procedure and can even be mechanized, e.g. if connected to the locking step. With suitable such control the same mechanical means can be used both for cartridge movement and subsequent dosing which strongly simplifies internal design.

Further objects and advantages with the invention will be evident from the detailed description hereinbelow.

DETAILED DESCRIPTION

The principles of the present invention may be used for injection devices or systems in broad terms for any type of chemicals, compositions or preparations delivered for any purpose. The invention has been developed mainly in view of applications for medical preparations and for convenience the invention will be described in terms of this use. In these applications an infusion channel or conducting means may be a tube or catheter, a needle or cannula or a needle-less system based on liquid jet or a particle gun with fluid propellant. The material in the cartridge shall be ejectable by a displacement of the movable wall and any material fulfilling this requirement can be used. Normally the material is a fluid and preferably a liquid, including materials behaving as liquids such as emulsions or suspensions. These observations relates to the final preparation whereas other components, notably solids, may be present before final preparation. The nature of cartridge content shall also be understood to include pharmaceuticals in broad terms and to embrace for example natural components and body fluids pre-filled or drawn into the cartridge although most commonly the pharmaceutical is factory prepared. The invention gives particular advantages in connection with sensitive compounds susceptible to degradation or denaturation under mechanical stress such as high shear forces. Compounds of high molecular weight may be of this type, high molecular weight hormones for example growth hormones. The invention also offers special advantages in connection with pharmaceuticals requiring a preparation step immediately prior to the infusion, typically a mixing of two or more components, which all may be fluid or may include a solid as when dissolving a lyophilized powder in a solvent, such as hormones or prostaglandins.

The administration manner can also be varied within broad limits and may include entirely continuous infusion, continuous infusion with varying flow or intermittent infusions or injections with repeated either equal or varying doses. Especially when combined with automation means to be further described below the administration manner can easily be varied by adaptations in software or similar control. Yet the invention give special benefits in intermittent administration. Similarly the invention give advantages, e.g. in initiation, in most administration manners also when only a single dosing operation is contemplated, although special advantages are obtained when the cartridges are designed for more than one or multiple individual doses for intermittent administration.

As stated, the infusion device type forming the basis for the current improvements includes at least a cartridge for the pharmaceutical preparation, a housing for at least a dosing mechanism and a piston rod in broad sense operable to engage and displace the cartridge movable wall.

A cartridge for the present purposes may generally be said to include a vessel having a front part and a rear part defining a general cartridge axis, an outlet for the preparation arranged at the front part and at least one movable wall arranged at the rear part, a displacement of which wall causes the preparation to be moved towards or expelled through the outlet. Vessel shape and movable wall have to be mutually adapted. The vessel may be designed most freely when the wall is a flexible or oversized membrane or diaphragm able to adapt by movement or reshaping to vessel internal surfaces, in which case a fluid cushion or resilient material may be needed between the wall and piston rod to smooth out applied pressure. Preferably, however, the vessel has a substantially constant internal cross-section, with a similarly constant vessel axis, between front and rear parts giving a generally tube-shaped vessel, and most preferably the cross-section is of the common circular type giving a substantially cylindrical vessel. The movable wall is then preferably a substantially shape-permanent, although possibly elastic, body sealingly adapted to the internal vessel surface and preferably of the plunger type having sufficient length to self-stabilize against tumbling during travel along the vessel. The front part outlet may be of any known design and directed laterally for best access in certain applications, frontal but non-coaxial with vessel axis or most commonly arranged frontal and coaxial. The outlet may be integral with the vessel or in a conventional manner the cartridge front end may be provided with an attachment therefore and before connection be provided with a breakable or penetrable sealing.

Generally the described cartridges need several kinds of initiation actions, dependent on a displacement of the movable wall, to reset the device and make possible repeated and reproducible dosing meeting high precision demands. In its first movement the movable wall may need an extraordinary break-loose force after storage to overcome both internal reshaping resistance and an increased wall friction due to adherence or depletion of lubricant in contact points. Also in relation to the weaker regular injection force, elastic and inelastic deformations and tolerances have to be evened out in the movable wall, cartridge shell, outlet attachments et cetera. The preparations themselves may have compressible inclusions such as gas vesicles. Deaeration and pre-ejection is needed to remove gas in the vessel compartment and fill out spaces for example at the front sealing, outlet attachments and the interior of the outlet devices or needles.

Dual or multi chamber cartridge types are known e.g. for preparations demanding a mixing of two or more components or precursors before administration. The components are kept separated by one or more intermediate walls of different known designs, which walls divide the vessel into several chambers, sometimes placed parallel along cartridge axis but most commonly in stacked relationship along the axis. Unification of the components may take place by breaking, penetrating or opening a valve construction in the intermediate walls, for example by introducing a pin or needle through the cartridge front, through or at the rear movable wall or by means at the cartridge exterior (compare e.g. the cited WO 93/02720). In another known design the intermediate wall or walls are of the plunger type and flow communication between the chambers is accomplished by moving the plunger to a by-pass section where the interior wall has one or several enlarged sections or repeated circumferential grooves and lands in a manner allowing by-flow of rear chamber content into front chamber at displacement of the rear movable wall (compare e.g. the cited U.S. Pat. No. 4,968,299 or WO 93/20868 and WO 95/11051). The chambers may contain gas, liquid or solids. Generally at least one liquid is present. Most commonly in pharmaceutical applications only two chambers are present and typically contains one liquid and one solid, the latter being dissolved and reconstituted during the mixing operation.

Initiation of the multi-chamber type cartridges requires all the general type steps described, although in aggravated form due to the additional walls and spaces present In order to provide for efficient mixing generally a mixing space has to be allotted in addition to the space occupied by the component volumes. Powdered components in bulk form also require the extra space contained in interstices between particles. The mixing step may produce foam or gas inclusions requiring space to settle out. Plunger type intermediate walls generally have to be displaced at least their own length to reach the non-sealing site in the by-pass. In total multi-chamber type cartridges require long movable wall strokes in the initiating step, both for mixing and subsequent deaeration, and benefits in a particular way from the advantages of the current invention.

Cartridge sizes may vary strongly depending on the intended application and general ranges are difficult to give. Typical sizes in the preferred self-administration application by use of portable devices are 2 to 30 mm internal diameter and preferably 3 to 20 mm. It is desirable to have a large length to diameter ratio, say between 2 and 20 and preferably between 2.5 and 15, based on the preparation column after initiation but before any dosing or dispensing. Cartridge lengths are clearly larger due to at least piston dimensions, in the case of multichamber cartridges considerably larger for reasons stated, but their length to diameter ratio is preferably kept smaller than 20 times and preferably less than 10 times the above stated column ratio.

In addition to the minimum cartridge features described above the present invention may require some design structures facilitating gripping, moving and locking. To a limited extent such structures can be placed at the interior surface of the cartridge vessel. In many instances, however, it is preferred to use the vessel exterior. A single-wall cartridge may still be used, especially when using machineable or moldable wall materials such as glass or polycarbonate. Better design flexibility is obtained with separate parts on the exterior side of the cartridge vessel. These may be limited to the positions needing the special structures mentioned or can embrace virtually the entire vessel (compare e.g. U.S. Pat. No. 5,435,076) to form a sleeve or container for the vessel, for example to provide additional protection or to make possible a free choice of fixation sites for the vessel. The container may be given a snug fit over the vessel for best guidance and smallest size or may leave some play therebetween, for example in order to accommodate vessels of different shape, diameter and length, or allow the vessel to freely rotate therein. Structures for the abovesaid purposes may include areas of increased friction suitable for gripping or sealing, splines or other shapes of non-rotational symmetry to prevent rotation but allow axial displacement, internal or external threads to either lock the cartridge or move it by use of an actuator with mating threads, flanges or protrusions for gripping or locking, sockets or seats for gaskets etc. Details in these respects will be discussed below in relation to each function embodiment. On the sleeve or container parts in particular may be required that they comprise windows or are made of transparent, translucent or other material allowing visual inspection or automated sensing of the vessel or vessel content or any coding thereof. The separate parts, sleeves or containers here described are supposed to follow the vessel in at least its axial movements. Accordingly, whenever used herein the concept "cartridge" shall be understood to include any part designed to accompany the vessel at least partly in its axial movement relative the housing between gripping and locking.

The device housing represents the point of reference for the cartridge movement and the piston rod movements and also the point of reference for forces applied by actuating means performing said movements, whereat the force is applied between the housing and the moving or gripped part. The minimum functional requirement is that the housing offers a support or platform for the movable parts and the actuating means providing the movements and forces. As in common practice, however, it is preferred that the housing forms a container at least partly embracing the parts and preferably also to such an extent that only the features designed to be controlled or monitored by the operator are externally exposed.

Arranged at or in the housing are at least the piston rod, the gripping means, the locking means and the actuating means for movable parts. As will be further discussed below additional means may be present, notably controlling and sensing means.

Although the housing can have a size large enough to extend beyond the cartridge after gripping and before movement, and accordingly the movement takes place entirely over or within the housing, it is preferred in order to conserve size that, in the direction of the cartridge axis, the housing ends proximal to the cartridge distal end before cartridge movement. In said direction and before movement the cartridge accordingly forms the distal part of the entire device. Also after the movement and when the cartridge is in the locked position the housing may end clearly proximal to the cartridge distal end or front part, for example to save weight or facilitate visual inspection. Since the abovesaid size conservation considerations do not apply in the rear or locked position, it may be preferred to extend the housing at least partly, and preferably substantially totally, along the cartridge in this position, for example to protect the cartridge, to provide guidance for the cartridge during movement or in its final position or to provide a site for sensing or detecting devices to be further explained below. The housing may here be given a tube-shape, substantially or totally surrounding the cartridge, possibly with window openings, having an opening at its distal end adapted to cartridge shape and size. Also in the absence of the abovesaid extension of the housing, when the housing ends clearly proximal to the cartridge distal end, it may be advantageous to provide a similar opening, especially when the housing in the preferred manner is shaped as a container. Accordingly it is a general preference to provide an opening in the housing, which opening surrounds the cartridge in whole or in part and in size and shape allows the cartridge to be received and to perform at least part of its axial movement therein. Although conceivable that a housing part extends into the interior of cartridge vessel or between the vessel and an outer part, it is preferred that the whole of the cartridge as defined is embraced by such an opening.

Whenever desirable to minimize device overall size the housing parts extending in the direction of cartridge axis but opposite the cartridge receiving end of the housing should be given an as short extension as possible. Rarely device dimensions before or during initiation is a major problem to the user and the point of reference for size evaluations hence is the situation after initiation and before dispensing. In the present device the critical measure may also be taken when the cartridge has been locked to the housing. This measure may preferably be constant during the injection operations or may decrease in case the device is allowed to shorten in accord with preparation consumption, as known per se, and in the latter case the point of reference should be before first dosing operation. In said situations a first value of interest is the maximum housing length along cartridge axis, or parallel thereto, when measured from the rear end of the cartridge. Preferably said distance is between 2 and 20 cm. better between 3 and 15 and most preferably between 4 and 10 cm. A second value of interest is the first value related to the total dosing stroke length desired from the cartridge type used. Said ratio is preferably at least 1, often at least 1.2 and preferably at least 1.5 but less than 10. better less than 7 and most preferably less than 5. Maximum device dimension perpendicularly to cartridge axis is generally less than the maximum coaxial dimension.

The piston rod acts to engage and displace the cartridge movable wall and is at least partially arranged in or at the housing. At least during dosing operations the piston rod shall be axially movable relative to the housing between one or more retracted positions and one or more extended positions relative the cartridge outlet. The piston rod may also be arranged to move axially during cartridge movement, either to increase or decrease its motion relative the cartridge, for example in connection with engaging or disengaging operations in the beginning or end of the movement or in order to fine-tuning displacement of movable wall for different initiation phases during said cartridge movement. It is generally preferred, however, to maintain the rod substantially axially stationary in relation to the housing during cartridge movement, which allows for smallest size and least elaborate mechanical design, and instead use the gripping means for control of cartridge movements. In its retracted position the piston rod or parts connected thereto may extend beyond and be exposed at the rear part of he housing, opposite the cartridge receiving front part, for example to minimize housing size, but is here preferably contained within the housing boundaries for safest and most convenient operation and for added space in case or further auxiliary functions. Similarly, even in a retracted position the piston rod front part extends into the cartridge interior after movement thereof and at least some of these parts may extend beyond housing boundaries at its front end, especially when the housing does not embrace substantial parts of the cartridge as above described, but may also entirely be within the housing, especially when the housing protrudes around the cartridge. The axial rod movements or restrictions described do not exclude that the rod may perform lateral or in particular rotational movements for other purposes to be discussed.

The piston rod shall be rigid enough to at its front end be able to displace the movable wall when actuated further back and shall at least be long and straight enough to extend through the cartridge interior with a possible additional length necessitated by actuating means. In other aspects the concept "rod" shall be understood in broad sense to comprise single or composite structures and details given thereto e.g. for actuation or control but shall generally exclude axially non-movable parts. The rod front end shall engage the movable wall in a manner allowing at least a pushing action, for which action no physical attachment to the wall is necessary but only an end surface or part abutment giving a desired even and distributed force, possibly via cushioning means as described. In case it is desirable to provide for a pulling action on the wall, for example to allow for aspiration of preparations or body fluids into the cartridge, the rod head engagement need to include a physical attachment to the wall which can be of any conventional or known type, such as based on friction, push lock, undercut, bayonet lock, threads or any other fit.

The arrangements for propelling the piston rod axially generally incorporates actuating means and suitable engagement features on the rod for transfer of the force thereto, which means and features have to mutually adapted and which can take a variety of forms to be exemplified below. It is initially observed that any engagement features mentioned can be placed either at the rod itself or on a separate shaft, e.g. substantially parallel to the rod, with a simple pushing arrangement therebetween, as exemplified in several of the references mentioned in the introduction. In order to save size and weight it is generally preferred to make the adaptations on the piston rod itself and for convenience the description will be given in terms of this option. The rod may be engaged simply by a clutch arrangement relying on friction, possibly amplified by a wedging action between radially affected wedge and a complementary shaped axial groove in the rod, on which the propulsive force is applied A simpler arrangement is obtained by providing the rod with an axial series of annular or single-sided transverse ribs, grooves or teeth engaged by meshing structures on the actuating means, for example a driven toothed wheel. Less strong forces need to be provided by the actuating means if the rod is threaded and driven by a complementary screw-and-nut arrangement, owing to the gear ratio obtained. The actuating means may then rotate the nut, for example over a gear mechanism, while the rod is prevented from rotation or the actuating means may rotate the rod itself, for example over a driving wheel attached thereto, while the nut thread is kept rotationally stationary. In all but the last of the above examples it may be desirable to lock the rod against angular displacement while allowing axial displacement. This can be done in a multitude of known ways incorporating a non-rotationally symmetrical detail on the rod, such as one or more flat surfaces, grooves etc. either on the rod exterior or in an axial bore therein, the detail extending with axially constant cross-section along the rod, or a non-rotationally symmetrical detail, such as a protrusion cooperating with a mating axial channel on a cooperating member such as a surrounding sleeve or on a shaft in an axial bore. The details may also act as bearings for the rod, either alone or in addition to separate conventional bearings. The details and bearings should assure a rod alignment substantially coaxial with the cartridge axis, possibly with tolerances allowing adaptation to minor misalignments therebetween.

The actuating means generally includes motor means and energy source. The "motor means" shall be understood to include any transmission needed to give the movement or function specified. The motor means can be of any known type, e.g. electric, hydraulic, pneumatic or mechanic. Electric motor means are preferred due to simplicity and ease of control. The energy source may be external and include means for energy transfer to the device but in order to make the device truly portable internal energy sources are preferred. For the present purposes the "energy source" shall be understood to include any transformation or conversion means necessary for delivering the energy in the form required by the motor means although it is preferred to select energy sources so as to limit such conversions within the device. The energy source can direct manual energy but preferably incorporates stored energy such as pumping means or a pressure source for pneumatic or hydraulic motor means or a spring system for mechanical motor means. For electrical motor means capacitors or preferably batteries are suitable energy sources. Several motors or several energy sources may be used, for example a combination of any of the means mentioned to drive different mechanical parts, instruments or sensors of the device, although it is generally preferred to use as few means as possible. When used herein "actuating means" shall be understood to include all necessary means for energizing the device unless special means are explicitly suggested.

The drive of the motor means may be applied to the piston rod at different locations. The motor means may be allowed to follow the rod in its movements, requiring only a single engagement spot on the rod. It is preferred, however, to make the motor means stationary. The engagement point can then for example be chosen close to the cartridge end, allowing engagement on the rod during the entire ejection phase and allowing the space behind to be utilized, e.g. to provide for a shrinking construction. The engagement point can also be selected at the opposite end at the rear part of the rod, which in case of stationary motor means requires some transfer means, for example a sleeve surrounding the rod, a shaft extending into an axial bore thereof or a pusher affected in a similar manner.

The minimum length of the piston rod, as defined, corresponds to the desired dosing stroke, possibly with an additional length to allow for the engagement features as described, for example at least 1.1, at least 1.3 or preferably 1.5 times the desired dosing length. The minimal length can be useful for example if the displacement of the cartridge movable wall during initiation up to start of dosing, at cartridge movement, is performed by an axially stationary plunger shaft whereafter dosing is performed by the axially movable plunger rod when extending from the front of the stationary part by use of any of the driving mechanisms described. Preferably the maximum length here substantially corresponds to the length of the stationary part. Generally a simpler and more precise construction is obtained if the piston rod is given a minimum length corresponding to the desired travel under both initiation and dosing or preferably its entire travel in the cartridge interior again with an addition length required for actuation, such as at least 1.1, at least 1.3 or preferably 1.5 times the said lengths. The maximum length is preferably less than 4 times, better if less than 3 times and preferably less than 2 times said lengths. If desired the rod can be made telescopic within these limits.

Generally the gripping means of the invention includes attachment means and moving means, with the proviso that the same means can perform both functions. The gripping means shall be able to attach, hold and retract the cartridge relative the housing. The gripping means may be entirely different from the piston rod means for example in order to permit a high degree of operation flexibility. They may engage the cartridge at the interior thereof in which case such means preferably at least partially surrounds the piston rod, limiting space requirements. They may also engage the cartridge outside the channel thereof, for example on the exterior or between vessel and possible outer parts, which allows for more narrow cartridge channels to be used. The gripping means may move the cartridge by carrying it rearwards in its own axial movement in the same direction or the gripping means may be axially stationary but provide a rotation which is translated into an axial cartridge movement by a screw-and-nut mechanism, whereat the cartridge may rotate vis-a-vis a stationary thread but preferably it is the other way around and the thread-bearing part is rotated while the cartridge is prevented from angular movements.

The length of the gripping means may correspond to the movement length for the cartridge, preferably with an added length for actuation engagement, which minimum length typically is used when the point of actuation engagement is close to the rear extreme of cartridge movement, but gripping means length may be extended further rearwards, especially when the point of actuation engagement is positioned further back, although it is preferred not to extend it much farther than the rearmost part of the piston rod in its retracted position. In the described actions any of the driving principles suggested for the piston rod can be employed. The actuating means may include separate motor means for the gripping means and the piston rod but it is preferred to use the same motor means and provide for a shift of engagement therebetween. Generally the piston rod can independently be controlled to engage and displace the movable wall in any operation pattern desired, the preferred pattern though being, as has been indicated, to retain the piston rod in a stationary position but with its front end in such a position relative the gripping means that it performs at least a part and preferably substantially all the movable wall displacement necessary for initiation, the stationary rod principle among others facilitating use of the same actuating means, with suitable shifting means, for both gripping means movements and piston rod movements.

In order to reduce the mechanics, save space and allow narrow cartridges in the system it is preferred to utilize the piston rod not only for affecting the cartridge movable wall but also as gripping means for cartridge movement A preferred way of implementing this objective is to allow the cartridge to move over and along the piston rod while the rod is in engagement with the wall. Preferably the relative movement between cartridge and piston rod is accomplished by a threaded engagement therebetween. Although conceivable that the cartridge is the driven and rotated part hereby moved along the threads of the piston rod part, kept at least rotationally stationary, a generally simpler design is possible if the piston rod is the rotated part and the cartridge is prevented from rotation while its axial movement is allowed, e.g. by any of the abovementioned means. The threads on the piston rod may be arranged on another rod part than the central part extending into the cartridge vessel interior, for example on a sleeve surrounding said central part which aids a free positioning of the cartridge threads, for example on the exterior thereof, and the central part can be unthreaded. Size requirements are reduced if the central rod part intended to at least partially extent into the cartridge vessel interior is equipped with the threads. The above design possibilities relates to the piston rod in its function as gripping means for the purposes of cartridge movement and at least partial initiation thereof. For purposes of the subsequent dispensing any of the earlier described motion principles for the piston rod can be employed, entirely independent of the now described gripping means features, for which a change of movement control may be needed. Yet actuation by similar means is facilitated if threads on the rod are used for both purposes. There are some advantages in using different thread types, e.g. left-handed and right-handed respectively, for the two operations, although a single and continuous thread has proved to give an especially smooth operation.

As initially indicated special attachment means may, but must not, be provided to affix the moving means to the cartridge. It is preferred that the housing or gripping means at least comprises guides for aligning an inserted fresh cartridge both laterally and axially in a position suitable for attachment. The movement means described may in themselves act to permit attachment. In a preferred embodiment of this option the rod and cartridge members are threadedly engaged which requires a minimum of assisting means for triggering attachment in an accurate fashion. One preferred assisting detail is to provide a positive pressure between rod and cartridge threads by applying force and resilience therebetween, preferably to the rod part, e.g. by a spring load. Another preferred assisting detail is to use a sufficient thread pitch to permit more than one, say two to four, independent and parallel threads, giving an equal number of circumferential engagement opportunities for the members, assuring a correspondingly accurate dispensing precision by control of rotation degree only, in the absence of which a more difficult monitoring of axial distances would be necessary. Still another preferred assisting detail is to design at least one of the opposing threaded terminal ends with inwardly tapering surfaces to assist coaxial alignment of the members. Yet another preferred assisting detail is to make one of the cooperating thread parts, preferably the female thread part, in a manner known per se, slightly resilient and with protrusions instead of complete threads, thereby having the capacity to accommodate the opposing threads in a multitude of angular positions, possibly also cooperating with a distinct stop surface between members for defined axial relationship. It should here again be emphasized that threads on the cartridge part can be provided on the cartridge vessel itself, either on its internal or external surface, or on a separate part of the cartridge, the latter opportunity being preferred for more elaborate configurations.

A different approach to the attachment problem, preferred when the available space so permits, is to design a carriage for the cartridge, which carriage forms a part of the cartridge in its travel, and accordingly is a detail of the cartridge in the above defined sense, but which carriage is more or less permanently attached to the movable means or at least does not require any separate attachment operation. In this embodiment any of the above described engagement principles between rod and cartridge can be utilized between rod and carriage. It is preferred that the carriage has guiding structures for locking the cartridge in a defined and stable axial relationship to the carriage and, whenever any of the abovesaid propulsion mechanisms so requires, also assisting a stable angular location of the cartridge, such as splines or any other structure of non-rotational symmetry. Any known locking means serving this purpose may be used. With suitable design the only step required by the operator of the device when inserting a cartridge or replacing an emptied cartridge with a fresh one is to secure a proper positioning of the cartridge in the cartridge and for this reason it is preferred to use simple locking means such as a push, screw, bayonet or any other similar known fit.

After movement of the cartridge the cartridge shall be locked relative to the housing, at least in respect of further axial movements but also preferably in respect of angular movements, by use of locking means of the device. Said locking means may take the form of any known type, such as screw, push, bayonet, solenoid-based etc. However, it is preferred to take advantage of the locking already provided by the gripping means in order to simplify the device and the operation thereof. When gripping means acting separate from the piston rod are present the minimum requirement is that these gripping means after cartridge travel keeps the cartridge stationary in relation to the housing and in this case the locking means are limited to the control features necessary for maintaining the stationary position. Yet it is generally preferred to add locking means in addition to such gripping means locking. It is preferred to add at least a stop surface on the housing against which a mating surface on the cartridge is positively abutted. A complementary locking against rotation can be provided with cooperating axial protrusions on the abutting part, by friction in case of treaded engagement, by a separately acting and controlled part such as a solenoid operated locking structure or in any other known way. Entirely separate locking means for the cartridge can with preference be used. e.g. for added locking safety, higher operational flexibility and especially when the piston rod is used as gripping means in order to relieve it for its dispensing task. Such means preferably lock against both forward and rearward motions and preferably also against angular movements, for which purposes any of the additional means mentioned above in relation to the separate gripping means can be used. Most preferred are locking means separately operable to lock in all three directions. The separate operation may be done with processor means or by mechanical means, e.g. being activated in a certain positional relationship between the device parts. The locking means may provide several locked positions along the cartridge movement trajectory, which option may be used to provide a shrinking device also during the device dosing or ejection phase. A convenient implementation for this purpose is to use gripping means separate from the piston rod and being arranged to move and stop the cartridge at several points to provide the several locked positions. A typical operation would be to move the cartridge towards the housing to a first locked position, make a forward expulsion movement with the piston rod, move the cartridge towards the housing to a new locked position, make a new expulsion rod movement etc.

Cooperation between the device parts has been indicated in relation to the various embodiments given, suggesting that a number of operational possibilities are available. In broad terms the preferred operation manner is to move the cartridge, with its rear part leading, relative the housing while keeping the piston rod substantially axially stationary relative the housing and during at least a part of the movement engaged to and displacing the cartridge movable wall to perform at least partial initiation thereof whereafter the cartridge is kept stationary in relation to the housing while the piston rod is axially moved in relation to the housing and in engagement with the movable wall to perform at least one dispensing action. Formally an initial step may be to orient the cartridge with its front part distal and its rear part proximal to housing. As has been indicated the cartridge movement may be intermittent or continuous with varying or preferably constant speed. It is an advantage of the invention that the movement can be controlled for each purpose in the initiation and that a slow and even motion can be provided where needed, for example in the mixing of components in dual or multi chamber cartridges. Similarly the dispensing action of the piston rod can be intermittent or continuous with constant or varying speed depending on the infusion type and administration pattern desired. From this follows that a single dispensing action to empty the cartridge is possible although most often several individual actions are desired at which each dose may be equal or individually set. Although possible to retract the piston rod from the movable wall between each dispensing action in intermittent dispensing, for reasons and in a manner known per se, which can easily be done with software control, it is generally preferred to maintain the piston rod substantially engaged or abutted with the movable wall between individual dispensing actions.

A special safety advantage is obtained if means are provided or precautions taken to prevent cartridge release during intermediate operation stages. If it is possible to remove the cartridge for example during the dispensing phase and reinsert the same or another cartridge a dangerous situation may occur due to loss of control over type and amount of preparation expelled in the dispensing actions to follow. Preferably then, release of the cartridge is prevented at least when the piston rod is in position for dispensing, preferably also prevented during initiation of the cartridge and most preferably also as soon as movement of the cartridge relative the housing has started. Expressed in another way it is preferred that whenever the operation of the device has started from a reset point from which the various operations take their reference, release of the cartridge shall not be possible until the device has returned to the same reset point. A preferred reset point being with the piston rod in its retracted position and with the cartridge in its distal relationship to the housing. In normal operation of the device between the starting reset point and return to the same reset point the cartridge has been initiated and at least substantially emptied by one or several dispensing actions before retraction of the piston rod and disengagement of the cartridge by movement thereof to the distal position. It is preferred, however, that the running operational cycle can be voluntarily interrupted and the device be brought back to the reset point, e.g. for correction maneuvers. The release prevention can be accomplished by processor control means but it is preferred that mechanical means are used. In this respect the present invention offers assistance since already at the cartridge movement step the piston rod projects into the vessel interior and the only further requirement is a locking against axial movement away from the housing, which is provided for other reasons as has been explained and exemplified.

The operational sequence preferably includes steps and means for commanding a shift between the various phases. In particular it is desirable to provide for controlled shift from the initial movement phase for the gripping means, when the cartridge is approached the housing, to the dispensing phase, when the piston rod is moved to expel cartridge content. Accordingly it is preferred to provide shifting means operative to end, and preferably also block, the movement of gripping means through a disabling action, possibly also assisting in the physical locking of the cartridge and accordingly being part of the locking means, and operative to release the piston rod for dispensing through an enabling action. Preferably these actions are reversible to permit, e.g. when a cartridge has been emptied and the piston rod has been retracted to its position before first dispensing action, the inverse operation of stopping, and preferably also blocking, piston rod movement through a disabling action and releasing the gripping means to remove the cartridge relative the housing through an enabling action, possibly also assisting in physical release of the cartridge. It is further suitable that the disabling and enabling respectively takes place substantially simultaneous, in case of software control by timely close signals and in case of mechanical control by physically connected device parts, although even so in the mechanical case a small play should be allowed in the chain from triggering event to enabling/disabling action in order to permit a large enough shift movement in the latter step. It has also been found suitable to link said disabling and enabling actions to the locking of the cartridge, either in its last/first movement relative the housing or to the actual locking/release of the cartridge.

The above control shift can be made entirely by software means for highest flexibility, provided the actuating means present are complete enough to individually drive the various parts in their intended movements, such as separate motor means and solenoid operated locking and blocking means. To secure operation in correct spatial relationship between parts, sensors or micro-switches may also be needed at critical positions for moving parts, e.g. for sensing the distal and proximal extremes for piston rod and gripping means. It is often preferred, however, to provide mechanical means assisting shift of control for safest operation and may be necessary if the same motor means are to be used for different purposes, such as movement of gripping means and subsequent movement of a separate piston rod, or if the piston rod shall be able to perform both functions. Mechanical shifting means can easily be placed so as to be triggered by the moving parts at the critical positions. Nothing prevents use of combined software and mechanical means for highest safety and operation redundancy.

Triggering of the abovesaid shift of control generally requires a sensing of the position for the relevant part used as triggering event and communication of this information to the enabling and disabling means respectively. A preferred triggering event for shift from cartridge movement operation to dispensing operation is cartridge arrival to about or precise its intended locked position relative the housing. Similarly, at the end of the full or interrupted operation cycle, when a reversed sequence may be desired, a preferred triggering event is the arrival of the piston rod at about or precise its retracted position corresponding to that immediately before dispensing. The actual sensing can be made in different ways such as by microswitches when electrical communication is desired or mechanically by for example an axial movement of a structure following the axial movement of the triggering part, a transformation of said triggering part axial movement into a radial movement e.g. by use of tapered surfaces or cam surfaces, a transformation of said axial movement into a rotational movement of a sensing part either with its axis parallel or perpendicular to the moving part axis, by use of a helical, e.g. screwing, cartridge movement for transformation of its rotational movement into a lateral sensing movement, e.g. by a protruding lug or cam surface on the cartridge, by the entering of a biased locking member into a slot or notch of the moving part when in the sensed position or in any other way. Any portion of the moving part, such as the cartridge, gripping means or piston rod, can be used for sensing, such as its front portion, its rear portion or an intermediate portion, provided the corresponding sensing part is so located that they cooperate when the part is in its intended triggering position, although it is preferred to use substantially the foremost and rearmost portions of the parts for this purpose.

Communication of the sensed triggering event to the enabling and disabling means respectively also can take a variety of forms. In software control said communication can be provided by the processor means. In the preferred use of mechanical control mechanical means are also used for the communication. The parts themselves may carry the information. For example the gripping means or the piston rod when used also as gripping means may sense the increased movement force when the cartridge abuts a stop surface and the increased force may by used to disable gripping means movement and enable piston rod movement for dispensing. It is generally preferred to use mechanical communicating means independent from the parts controlled by the enabling and disabling means themselves. The communication means can have different design as long as it performs the enabling and disabling action desired. If the gripping means and piston rod have independent motor means the communication means may enable and disable these motor means. If the same motor means are used for independent gripping means and piston rod the communication means may disengage the motor means from one of the parts and engage it with the other part. If the piston rod also performs the gripping means function it is preferred that the communication means acts to axially lock the cartridge while releasing the piston rod or vice versa, preferably with the motor means permanently engaged.

The device of the invention may be combined with additional optional features for improved performance. The device may be equipped with position sensing means to allow operation in certain orientations of the device but prevent operation in other. It is for example desirable that many of the steps in the initiation step, such as deaeration, pre-ejection and possibly also reconstitution, is made with the needle end pointing somewhat upwards and the position sensing means may assist in preventing activation or operation of the motor means for the gripping means or piston rod at a predetermined angular deviation from the desired upward orientation. The position sensing means may take the form disclosed in our copending Swedish patent application SE 9503685-1, incorporated herein by reference.

It is further preferred that the device is equipped with sensor means for at least one parameter of the cartridge inserted. The sensor may check for cartridge type in order to prevent use of cartridges of non-intended mechanical type, preparation filling or concentration. The sensor may also check for and possibly read a machine-readable coding of the cartridge. The sensor may also check for cartridge condition or status in order to alarm the user or prevent device operation in case any improper condition is detected, such as cracks or other mechanical cartridge defects, improper position or appearance of pistons or walls, incomplete filling, discoloration, presence of dirt etc. The present invention provides for certain advantages in connection with such sensors. Owing to the cartridge movement relative the housing it is possible to obtain a scanning action along cartridge axis even from a sensor stationary in relation to the housing and to use the same sensor for several measuring tasks. It is possible to adapt cartridge movement speed to that required for sensor measurements and for example allow for discontinuous travel and stops at critical locations. As at least partial initiation of the cartridge takes place during the movement it is possible to follow the development of a real-time event, such as the proper completion of reconstitution or successful deaeration. Although possible to use moving sensors it is preferred to use a stationary sensor for reasons stated. The position sensing means may take any of the forms disclosed in our copending application of even date entitled "Delivery device and method for its operation", incorporated herein by reference.

As indicated the injection device may be provided with processor means to perform the operations stated but also additional functions. Preferably the device is equipped with control means in the form of keys or otherwise for inputting necessary commands. After insertion of a fresh cartridge the gripping means may be enabled for movement automatically but it is preferred that the user enters a command to start the process of cartridge gripping, movement and initiation. The enabling may be dependent on that optional position sensing means reports proper angular orientation of the device as described. During cartridge movement and initiation the processor means may monitor output from any sensor present to trigger an alarm or interrupt or reverse the operation if any faulty condition is detected. If shift or command between the various phases described are processor controlled it may be necessary for the processor to receive input about the spatial positions of the parts and when the cartridge is at its locked position output a disabling command for the gripping means, possibly also a locking command to separate locking means, and simultaneously or later an enabling command for the piston rod dispensing action. With suitable design of mechanical means for shift of control as described it may be sufficient for the processor to start the process and stop it when the piston rod has been enabled for dispensing action, possibly after an initial dispensing action for completed deaeration or pre-ejection if not included in the initiation scheme. Before administrative dosing and dispensing the desired dose should be set either individually for each injection or for repeated equal doses. This dose setting can be preprogrammed into the device, possibly with processor controlled adaptation thereof to the cartridge concentration and type sensed, or it can be manually programmed by the user, possibly with a similar processor assistance. At least one user operated trigger or key should be present to initiate each dispensing administration at the activation of which it is preferred that the processor energizes the motor means for the piston rod to perform the required axial displacement. Preferably feed-back means are provided to register either the actual axial displacement of the rod or, with preference for best resolution, the actual angular rotation of the motor or the piston rod when rotational movements are present. It is also preferred that the processor keeps track on the total volume dispensed or the total piston rod axial displacement made for correlation thereof to the cartridge total available in order to prevent triggering of incomplete doses at the end of cartridge capacity. In addition to this a physical sensing of the piston rod extended extreme may be provided, either in absolute terms at a certain location or in terms relative the cartridge e.g. by sensing the additional force when driving the piston rod against the cartridge end. Any of these means may be used to, either automatically or after a manual confirmation, start the reverse operation of retracting the piston rod, disengaging the cartridge from the locking means and movement of the cartridge to its distal extreme, all in order to bring the device back to its start or reset point. It is also preferred that the device has an interface for connection to external data processing means, either for inputting data to the device or for downloading information from the device, for example time and dose amounts administered.

Preferred embodiments of the invention will be describe hereinbelow in relation to the drawings.

SUMMARY OF DRAWINGS

FIGS. 1A to 1C show schematically basic device features in three different operational stages.

FIG. 2 shows a similar device as in FIG. 1 with more detailed separate gripping means.

FIGS. 3A to 3F show a device based on separate gripping means and mechanical shift of command means wherein FIGS. 3A to 3D shows various operational stages and FIG. 3F shows details of the device.

FIGS. 4A to 4E show schematically a device based on a combined piston rod and gripping means part in different operational stages.

FIGS. 5A to 5E show a schematic modification of the embodiment of FIG. 4 designed to provide automated mechanical shift of command means.

FIGS. 6A to 6D show still another device based on a combined piston rod and gripping means and with mechanical shift means.

DESCRIPTION OF DRAWINGS

Figure 3A:
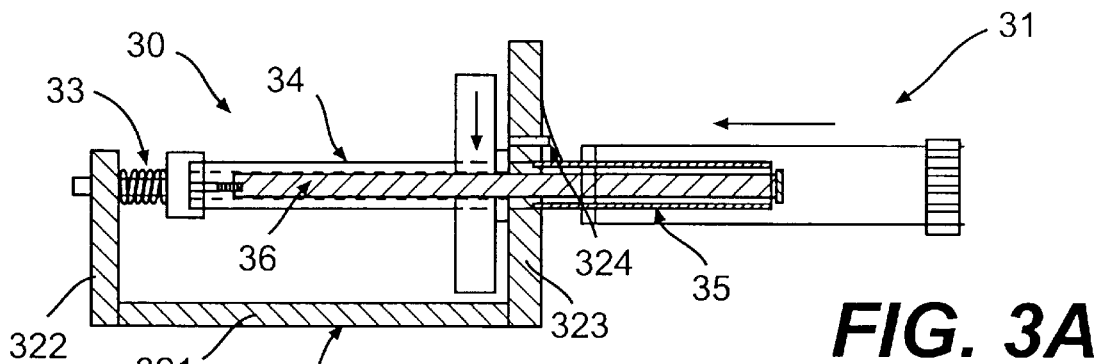

FIGS. 1A to 1C show schematically basic device features in three different operational stages. A cartridge, generally designated 1, has an elongated barrel 2, a front end 3 with an outlet 4, an open rear end 5 and a piston 6 displaceable along the barrel interior. More pistons may be present in case the cartridge is of dual or multichamber type. A pump or dosing device part, generally designated 10, comprises a housing 11, a piston rod 12, gripping means 13, locking means 14 and actuating means unit 15, shown in phantom lines. The piston rod 12 is operable to abut and displace piston 6 and is movable in relation to the housing. The gripping means 13 are designed to engage cartridge 1 and to move the cartridge, at least in the direction towards the housing with cartridge rear end 5 leading. The locking means 14 limits the cartridge movement and may further secure its positioning. The actuating means unit 15 are generally actuate the piston rod 12 and the gripping means 13 to perform their respective movements and contains shift of command means to secure the proper sequencing therebetween.

In the stage of FIG. 1A it is supposed that a fresh cartridge 1 has been attached to the device 10 in such a way that the gripping means engages the cartridge and that the piston rod, being at its rearmost extreme, is close to or abutting the piston 6 in its initial location in the fresh cartridge. FIG. 1B shows the relative positions when the gripping means 13 has moved the cartridge 1 into the housing 11 until its further movement in this direction is prevented by locking means 14. The piston rod 12 has been maintained at its rearmost extreme but still caused the plunger 6 to be displaced towards the cartridge 1 front end as a result of the cartridge 1 movement towards the piston rod 12. During this stage expulsion of medical through opening 4 can take place but preferably an initiation operation is performed. In the stage of FIG. 1C piston rod 12 has moved forward in relation to both the cartridge 1 and the housing 11 while cartridge 1 has been maintained stationary in relation to the housing 11 at the locking means 14. As a result piston rod 12 has moved the piston 6 to its foremost position in barrel 2 and the piston rod may be in its distal extreme position. During this stage the content of cartridge 1 may have been ejected through opening 4. The various actions has been coordinated in actuating means unit 15. It is contemplated that the reverse sequence may take place to enable a new fresh cartridge to be used, i.e. retraction of piston rod 12 to the position of FIG. 1B, release of locking means 14 and movement of cartridge with its front end 3 leading away from the housing 11 by actuation of gripping means 13.

FIG. 2 shows a device 20 similar to that of FIG. 1, and with common features having the same numerical references, but with separate gripping means of greater detail. The gripping means comprises a sleeve 21 with internal threads at 22, which sleeve is axially fixed in housing 11 but is rotatable by influence from actuating means unit 15. Cartridge 1 has corresponding external threads 23 but also longitudinal splines in the threads cooperating with mating splines structures 24 on a housing front surface 25. Locking means 26 are here arranged as lateral internal surfaces on the rotatable sleeve 21. Piston rod 12 is and acts similar to the piston rod shown in FIG. 1. The operation stage in FIG. 2 is in between those shown in FIGS. 1A and 1B respectively, i.e. the cartridge has been drawn into the housing 11 but shall be moved further to reach the locking means 26. The gripping means of FIG. 2 operates by rotation of sleeve 21, which causes the cartridge 1 to be axially displaced through the interengagement between sleeve 21 inner thread 22 and cartridge 1 outer thread 23, whereunder the splines at 23 and 24 respectively prevents the cartridge 1 from angular movements relative housing 11. The movement may continue until cartridge 1 abuts locking means surface 26, where the locking strength may reach any level through the bolting effect obtained. Rotation of sleeve 21 in the opposite direction will release cartridge 1 and displace it away from housing 11. As described in FIG. 1 the piston rod 12 may be kept fixed at its proximal extreme during gripping means operation.

Figure 3B:
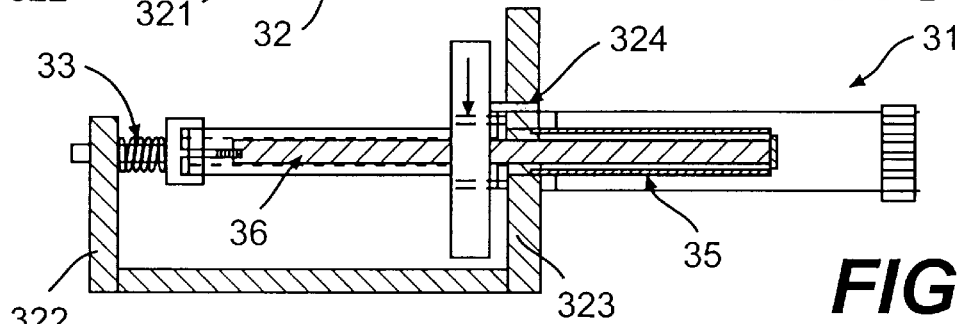
Figure 3C:
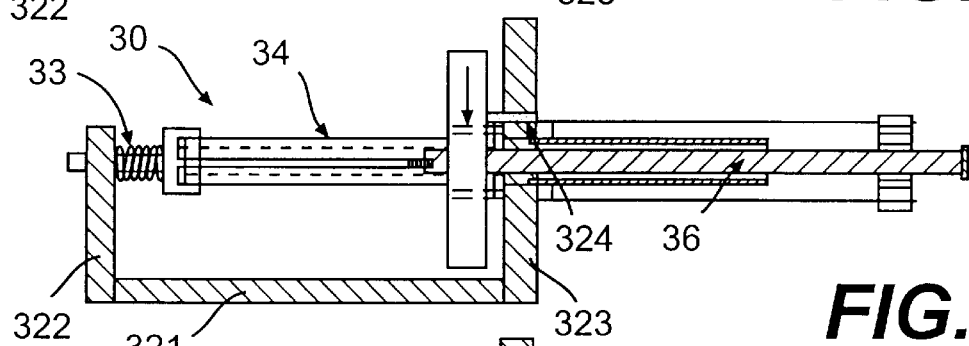
Figure 3D:
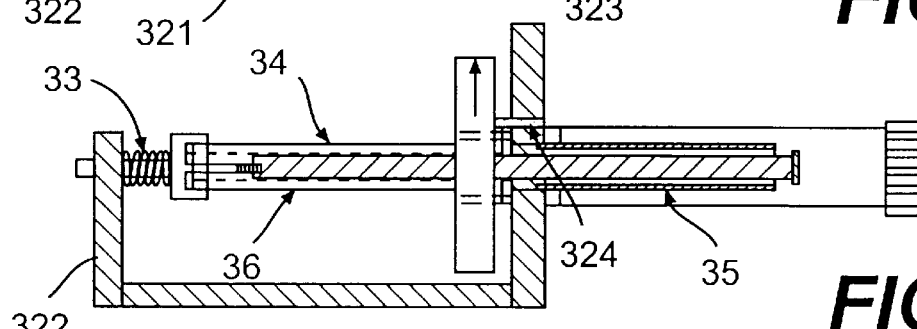
Figure 3E:
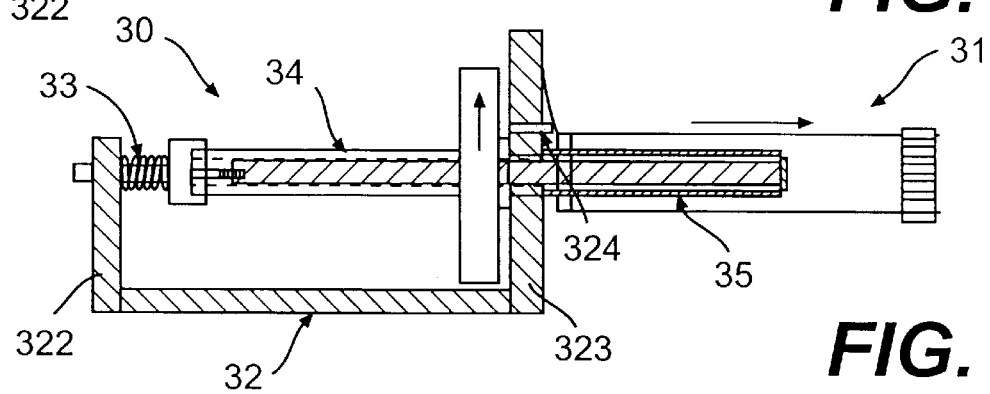
Figure 3F:
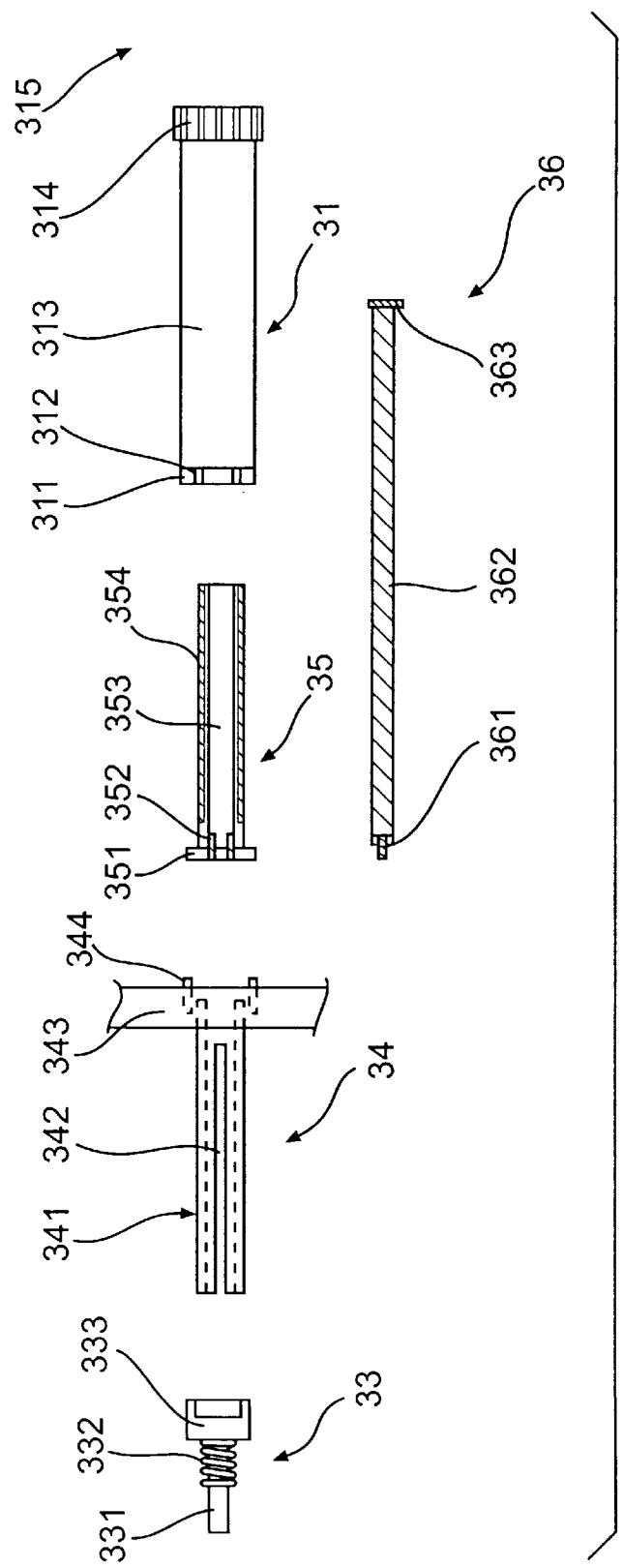

FIGS. 3A to 3F show a device based on separate gripping means and mechanical shift of command means, wherein FIGS. 3A to 3D shows various operational stages and FIG. 3F shows details of the device. In FIGS. 3A to 3E are shown a dosing device part 30 and a cartridge part 31. The device part comprises a housing 32 of chassis type, having a floor 321 and two vertical walls 322 and 323 with bearing holes for movable parts. A spring biased locking pin 324 is arranged at wall 323 close to its bearing hole. The movable parts include a spring loaded axis end part 33, a driver 34, a threaded sleeve part 35 and a piston rod 36, which parts are further detailed in FIG. 3F. The axis end part 33 comprises a shaft pivot 331, a spring 332 and a socket 333 for the driver 34 end. The driver 34 comprises a tube 341, adapted to receive the piston rod 36, with a guiding slit 342, a pinion wheel 343 and coupling pins 344 for connection to the threaded sleeve 35. The threaded sleeve 35 has a flange 351, with structures to receive coupling pins 344, internal threads 352 close to the flange, a tube part 353 and external threads 354 on the tube part. The cartridge 31 has a rear end 311, internal threads 312 at the rear end, for cooperation with external threads 354 on sleeve 35, a container part 313, splines 314 and a front end 315 extending to the right. The cartridge 31 shown may be a casing for a syringe barrel or in itself act as a syringe barrel. Piston rod 36 includes a follower pin 361, for cooperation with guiding slit 342, a rod shaft 362 with external threads and a pusher plate 363 for engagement with a plunger. Returning to FIG. 3A the assembly of the parts is seen. The axis end part 33 receives driver 34 end in socket 333 and the coupling pins 344 at the other end of driver 34 may or may not, to be further explained below, engage the corresponding structures in flange 351 of threaded sleeve 35. The threaded sleeve 35 is inserted through a hole in wall 323 so that its flange 351 abuts the inside of wall 323 and its tube part 353 extends away from housing 32. The sleeve 35 external threads 354 are adapted to cooperate with internal threads 312 of cartridge 31. Cartridge splines 314 are supposed to cooperate with mating structures (not shown) on housing 32 to prevent rotation of the cartridge 31. Piston rod 36 is inserted through driver tube 341 and through tube part 353 of threaded sleeve 35 so that follower pin 361 runs in guiding slits 342 of driver 34, to assure that piston rod 36 rotates with driver 34, and so that the external threads of rod 362 cooperates with internal threads 352 on sleeve 35, to assure that rod 36 is axially displaced when rotated in relation to sleeve 35.

The operation of the device is shown in FIGS. 3A to 3E. In FIG. 3A piston rod 36 is in its retracted position and cartridge 31 internal threads 312 are in engagement with external threads 354 of sleeve 35. Driver coupling pins 344 are in engagement with sleeve 35, with pressure from spring 332, and when driver 34 is rotated in the direction of the arrow on pinion wheel 343 driver 34, sleeve 35 and piston rod 36 all rotate together and cartridge 31 is drawn towards housing 32, owing to its threaded interengagement with sleeve 35 and its non-rotation provided by splines 314, in direction of the arrow above cartridge 31. In FIG. 3B the cartridge 31 has arrived to and abuts wall 323. At arrival it pushes spring biased locking pin 324 through its hole in the wall to displace driver 34, against spring 332, and to disengage coupling pins 344 from sleeve 35. Driver 34 and piston rod 36 are now free to rotate in relation to sleeve 35 and its internal thread 352. In FIG. 3C the continued rotation of pinion wheel 343 has caused piston rod 36 to move forward in an expulsion action through its screw-and-nut engagement with now stationary thread 352. In FIG. 3D the sequence is reversed by rotating the pinion wheel in the opposite direction as indicated by the arrow. The rotation has caused the piston rod 36 to return to almost its retracted position due to its engagement with thread 352. In FIG. 3E further rearward movement of piston rod 36 is prevented by contact between push plate 363 and distal end of sleeve 35 and the engagement at thread 352 then brings sleeve 35 to begin rotate with piston rod 36. The first disengagement of cartridge 31 releases locking pin 324, which is spring biased towards this position, and allow coupling pins 344 to permanent the connection to sleeve 35. Further rotation of pinion wheel 343 moves the cartridge 31 away from housing 32 in the arrow direction.

It is clear that in the just described embodiment the threaded sleeve 35 acts as gripping means, wall 323 as locking means, possibly together with the threads for bolting, and driver 34 acts as a part of actuating means for movement of both gripping means and piston rod. The actuating means also include shift of command means in form of the various control features described, which secure the desired sequence of stages and reduces control to a rotation of the pinion wheel in either one or the other direction, which can be made manually but preferably by an electric motor over gears. In FIG. 3B the triggering event is the arrival of cartridge 31 at wall 323 and communication thereof includes the locking pin 324 and the driver axial movement which in turn disables the gripping means and enables piston rod forward motion. In FIG. 3E the triggering event is the arrival of push plate 363 at sleeve 35, which is transformed to an enabling of gripping means and an disabling of piston rod.

FIGS. 4A to 4E show schematically a device based on combined piston rod and gripping means part in different operational stages. No housing is shown in the Figures but only the main movable parts. From right to left the device comprises a cartridge 41 having a midsection flange 42 with splines (not shown). A shaft 43, acting as both piston rod and gripping means, has a driving wheel 44, engaging e.g. flat surfaces on the shaft to permit shaft axial displacement therethrough, and a flange 45 at its rear. The shaft is externally threaded, aside from the flatted surfaces for wheel 44, and, as in the embodiment of FIG. 3, in engagement with a mating inner thread in cartridge 41, which cartridge is kept non-rotational by cooperation between the splines on flange 42 and similar structures on a housing. A shaft locker 46 is movable up or down behind the flange 45 to either release or prevent shaft 43 forward movements. A similar cartridge locker 47 is movable up or down behind the midsection flange 42 of the cartridge to either release or prevent its forward movement.

In FIG. 4A locker 46 is activated and rotation of the shaft 43 causes cartridge 41 to move in the arrow direction owing to the interengagement of shaft 43 external and cartridge 41 internal threads. In FIG. 4B the cartridge 41 has reached a rearward end position and locker 47 is now activated to prevent its forward movement while locker 46 is deactivated to allow forward motion of the shaft 43. In FIG. 4C continued rotation of shaft 43 in the same direction has moved the shaft to a forward extreme position within cartridge 41 but the rotation direction is now reversed to move the shaft 43 rearwards as indicated by the arrow. In FIG. 4D the shaft 43 has again reached its rearward extreme and locker 46 is activated to retain the shaft in this position while locker 47 is deactivated to permit cartridge 41 forward motion and continued rotation in the same direction as in FIG. 4C moves the cartridge in the arrow direction. In FIG. 4E the cartridge 41 has come to its foremost position and the situation is the same as in FIG. 4A. The cartridge can be replaced with a fresh one and the cycle reiterated.

This embodiment shows that the same means can be used as piston rod and gripping means. Shift of command is controlled by locks 46 and 47 which for example can be electromechanical operated, e.g. with solenoids, individually or in concert. A control system need only control the two lockers and motor forward and rearward rotation, possibly with sensors for detection of the shaft and cartridge extreme positions.

FIGS. 5A to 5E show the same general embodiment as in FIG. 4 although with some schematically illustrated modifications to provide a mechanical shift of command control. The numerical positions from FIG. 4 have been maintained. Shaft locker 46 and cartridge locker 47 have been given tapered lower surfaces and are placed under downward directed spring pressure as indicated by arrows 50 and 51.

This arrangement allows for cartridge flange 42 to pass under locker 47 and shaft flange 45 to pass under locker 46 when these parts move to the left in the drawing but prevent their movement to the right. As best seen in FIG. 5B a cartridge sensor 52, spring biased to the right as indicated by arrow 54, is arranged so that it is displaced to the left by the cartridge arriving at its rear extreme and this movement is communicated to the shaft locker 46, which is hereby lifted by the cooperation of ramp surface 53 and a corresponding surface on locker 46. The cartridge axial movement necessary for the lifting action is indicated at 55. As best seen in FIG. 5D a shaft sensor 56, spring biased to the right as indicated by arrow 58, is arranged so that it is displaced to the left by the shaft flange 45 arriving at its rear extreme and this movement is communicated to the cartridge locker 47, which is hereby lifted by the cooperation of ramp surface 57 and a corresponding surface on locker 47. The shaft axial movement necessary for the lifting action is indicated at 59. The features described are designed to eliminate the need for separate control of lockers 46 and 47 and reduce the necessary influence to a rotation of the shaft in either of two directions.

The operational differences relative FIG. 4 will next be described. The stage depicted in FIG. 5A operates in the same way as FIG. 4A, i.e. a rotation of shaft 43 causes the cartridge 41 to move to the left. In this embodiment cartridge locker 47 may slid along the cartridge until lifted by flange 42. In FIG. 5B cartridge 41 reaches its rearmost position and displaces cartridge sensor 52 to the left, hereby lifting shaft locker 46 to free shaft 43 for forward motion. In its movement the cartridge flange 42 also passes cartridge locker 47, which is first lifted and then falls in behind the flange to lock the cartridge against forward movements. FIG. 5C operates as FIG. 4C, i.e. a continued rotation of the shaft 43 in the same direction as before moves the shaft forward to expel cartridge content. Shaft locker 46 is kept high for the same reason as described in FIG. 5B as long as cartridge 41 is maintained in its rearmost position. In FIG. 5D, as in FIG. 4D, a rotation reversal brings the shaft 43 back to its rearmost position. Here it presses shaft sensor 56 rearwards which movement is transformed to a lifting action on cartridge locker 47, freeing the cartridge 41 for forward motion. In FIG. 5E continued rotation of shaft 43 in the same direction has brought the cartridge to the same position as in FIG. 5A. As soon as the cartridge left its rearmost position cartridge sensor 52 moved forwards, freeing shaft locker 46 which went low and blocked shaft 43 against forward motions. Cartridge locker 47 may be either high or low after passage of flange 42.

Figure 6A:
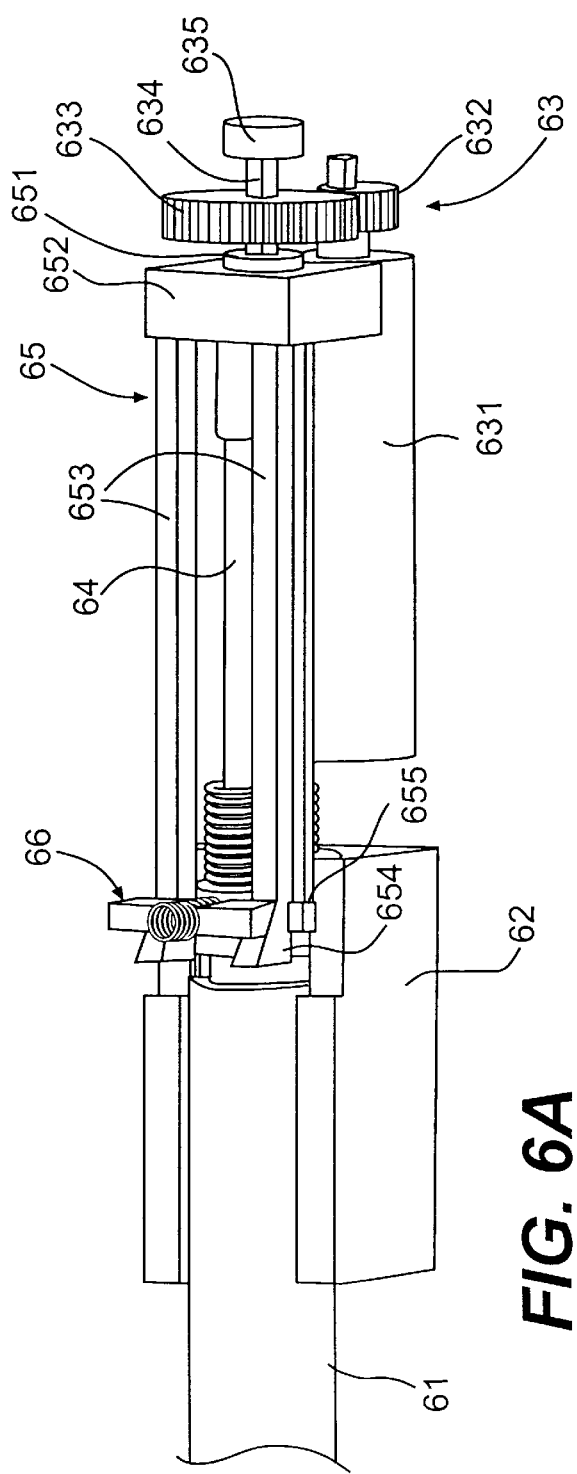
Figure 6B:
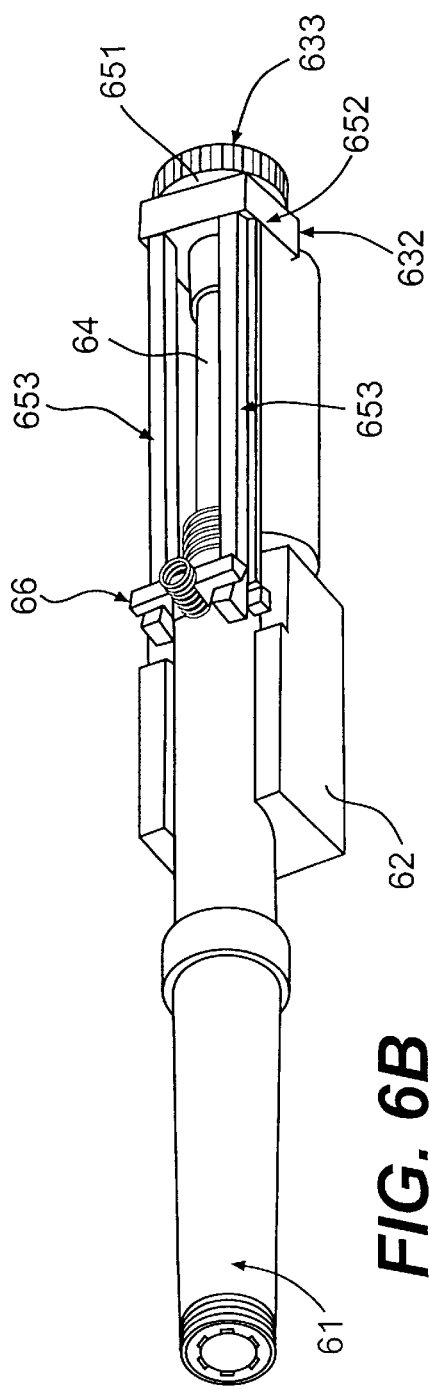
Figure 6D:
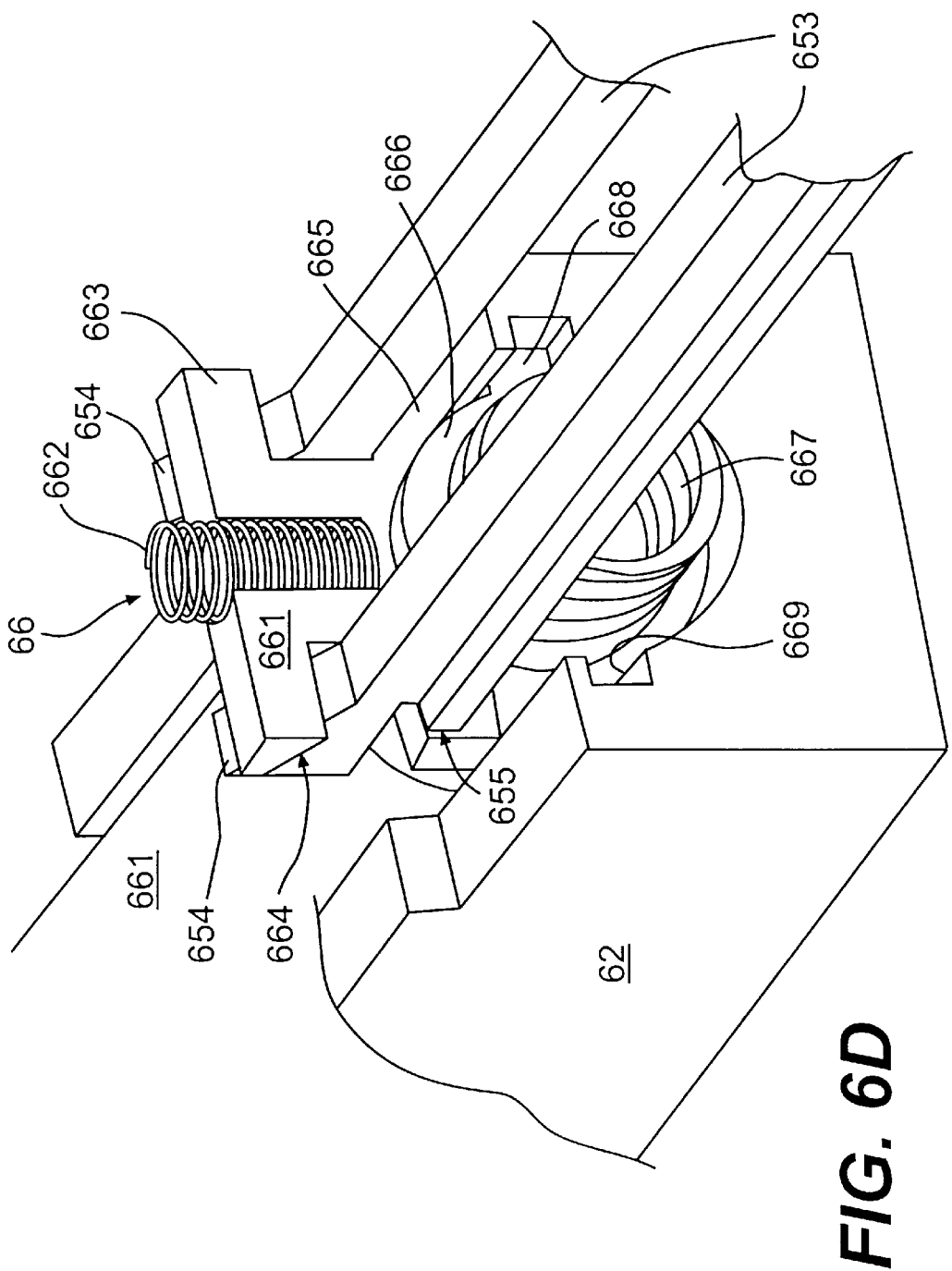

FIGS. 6A to 6D show still another device based on a combined piston rod and gripping means and with mechanical shift means. FIGS. 6A and 6B show two views of the device interior without housing. FIG. 6C shows the proximal part with neck of the cartridge used. FIG. 6D shows an enlarged view of the device locking and shift means. In FIGS. 6A and 6B are shown the cartridge 61, a guiding trough 62 connected to a housing, actuating means generally designated 63, a threaded shaft 64 acting as piston rod and gripping means, a shaft follower unit 65 and a locking mechanism 66. What is seen of cartridge 61 is an external shell housing in its interior a glass barrel of simpler design with at least one piston. As best seen in FIG. 6C the outer shell 611 has in its rear a flange 612 of slightly less diameter than the main part 611 and a neck 613 for engagement with locking means. The rear part opening 614 has internal threads (not shown) for cooperation with threaded shaft 64. Trough 62 has an inner contour of semi-circular cross-section, adapted the outer contour of cartridge 61. The actuating means 63 includes an electric motor 631 with a toothed wheel 632 cooperating with a larger toothed pinion wheel 633 attached to a pinion shaft 634, at the rear supported in a bearing 635 and in the forward direction extending into an elongated hollow cavity in shaft 64, the pinion shaft 634 and shaft 64 cavity being of mating but non-circular cross-section to allow the shaft 64 to be axially displaced with maintained actuation from the pinion shaft 634. Shaft 64 is threaded for cooperation with inner threads of cartridge 61 and its rear part is rotationally connected to follower unit 65. The follower unit 65 comprises a bearing 651 in wall 652 for the shaft 64 and two arms 653 protruding forward from the wall 652. As best seen in FIG. 6D arms 653 ends in upper ramps 654 and lower stop surfaces 655. The locking means 66 includes a lock piece 661, guided in the housing and being biased towards a lower position by spring 662. The lock piece 661 has an upper yoke part 663 with lower tapering surfaces 664, for cooperation with ramps 654 on arms 653, and a lower yoke part 665, which when raised cooperates with stop surfaces 655 on arms 653 to block arm forward movement Lower yoke 665 has a width adapted to enter neck 613, between barrel 611 and flange 612, of cartridge 61. The gap between upper 663 and lower 665 yokes are adapted to allow passage of arms 653. A rest ring 666 is slightly axially movable and biased towards a forward location by spring 667 and is stabilized in its movement by cooperating tags 668 on the ring and slits 669 in trough 62. Rest ring 666 is coaxial with cartridge 61 and has roughly the same diameter as flange 612 on cartridge 61 and is arranged to keep the lock piece 661 in its upper position when the ring 666 is in its forward location but allow lock piece 661 to be pressed towards its lower position, in neck 613, when ring 666 is pushed rearward by the cartridge flange 612.

The general operational pattern of the device of FIG. 6 is similar to that described in relation to FIG. 4, i.e. the shaft 64 is rotated in its retracted position to draw the cartridge 61 rearwards up to a locked position, the shaft 64 is then moved forward by continued rotation in the same direction to expel cartridge 61 content, the rotation is reversed to bring the shaft 64 back to its retracted position, the cartridge 61 is released and the cartridge 61 is moved away by continued rotation of shaft 64 in the same direction. The locking and shift means are different from those shown in FIG. 4 and their operation will be described in relation to FIG. 6D. At the moment depicted in FIG. 6D the shaft 65 (not shown) is in almost its rearmost position. The locking piece 661 rests against rest ring 666, allowing cartridge flange 612 to pass under locking piece, and lower yoke 665 is in engagement with stop surfaces 655 of arms 653 to block the follower unit 65 and the shaft 64 against any forward motion. Rotation of shaft 64 in the direction that attracts the cartridge rearwards will permit flange 612 of the cartridge 61 to pass under the lifted locking piece 661 to push away rest ring 666 and allow lock piece 661 to fall into cartridge neck 613 and simultaneously free shaft 64 for forward motion. Reversal of shaft 64 rotation direction will bring the ramped end parts 654 of arms 653 in engagement with the tapering surfaces 664 of upper yoke 663, causing the lock piece to be lifted out from the neck 613, permit flange 612 and rest ring 666 to pass under the lock piece 661 and again block the arms 653 against forward motion. A certain shaft axial play is allowed between the full enabling of cartridge movement and the full disabling of shaft movement.

An operation cycle may start with the shaft 64 in its rearmost position, in which the locking piece 661 is lifted to its upper position, secured there by rest ring 666 pushed forward by spring 667, blocking shaft forward motion but allowing passage of cartridge 61 flange 612. Even in its retracted position the shaft extends well beyond the locking mechanism 66 and to its end may be attached the cartridge by rotation of the shaft for engagement thereto of its inner threads. Shaft rotation will cause the cartridge to move towards the locking mechanism, pass with its flange 612 under locking piece 661, under simultaneous rearward displacement of rest ring 666, and be blocked from further axial displacement by contact between the locking piece and the larger cartridge main part 611. Locking piece 661 may now fall down into cartridge neck 613 to lock the cartridge and to completely free arms 653 for forward motion. Continued shaft rotation in the same direction will move shaft 64 and follower unit 65 forward to expel cartridge content. After expulsion, shaft 64 rotation is reversed and follower unit 65 and the shaft 64 move rearwards while cartridge 61 is still locked by locking piece 661 being in its lower position. When shaft 64 and follower 65 approach their rearmost position ramped end parts 654 of arms 653 come into engagement with the tapering surfaces 664 of upper yoke 663 and lifts the locking piece 661 against spring 662 pressure from cartridge neck 613, allowing rest ring 666 and cartridge flange 612 to pass under locking piece and so that lower yoke 665 is about in engagement with stop surfaces 655 of arms 653 to block the follower unit 65 and the shaft 64 against any forward motion. Continued shaft rotation in the same direction moves the now unlocked cartridge 61 forward, rest ring 666 moving in under locking piece 661 to secure its position, until the cartridge can be removed. It is clear that shaft 64 is disabled from axial movements as long as the cartridge is not in its locked position, with locking piece 661 in its lower position, and that the cartridge is disabled from axial movements until the shaft 64 and follower 65 are in their rearmost position, lifting the locking piece 661 to its upper position, and that no other control actions are needed than rotation of the shaft in either one or the other direction.

The exemplified embodiments are illustrative only and shall not be understood in any way limit the scope or generality of the invention as defined in the claims.

We claim:

1. An injection device comprising a) a housing, b) a cartridge containing a preparation or precursor components for the preparation and having a front part and a rear part defining a general cartridge axis, an outlet for the preparation arranged at the front part and at least one movable wall arranged between the front part and the rear part, a displacement of which wall causes the preparation to be moved towards or expelled through the outlet, c) a piston rod, having a first end and a second end, at least partly contained within the housing and being operable to engage and displace the movable wall at its first end and d) an actuator within the housing arranged to move at least the rod, a gripper connected to the housing and arranged to hold the cartridge, or an enclosure therefore, with its front part distal and its rear part proximal to the housing,
   the actuator being arranged to move the gripper so as to move the cartridge, with its rear part leading, relative the housing,
   a lock arranged in the injection device to lock the cartridge against axial movements relative to the housing, hereby defining a locked position for the cartridge,
   the actuator being able to move the piston rod between at least one retracted position and at least one extended position,
   a shifter at least operative to disable the actuator against axial movements of the piston rod relative to the housing during at least part of the gripper movement; and
   the relative positions between the piston rod in its retracted position and the cartridge in its locked position being such that the piston rod extends into the cartridge.

2. The device of claim 1, wherein the cartridge comprises a vessel having a substantially constant internal cross-section and that the movable wall is of plunger type.

3. The device of claim 1, wherein the cartridge is of dual or multi chamber type separated with one or more intermediate walls and containing component precursors to be mixed before administration.

4. The device of claim 1, wherein the cartridge comprises a vessel having an internal diameter between 2 and 20 mm and a length to internal diameter ratio above 3.

5. The device of claim 1, wherein the housing forms a container embracing at least part of the piston rod, the gripper, the lock and at least some of the actuator.

6. The device of claim 5, wherein the housing has an opening surrounding the cartridge in whole or in part and in size and shape adapted to allow the cartridge to be received and perform at least a part of its movement therein.

7. The device of claim 1, wherein the housing ends proximal to the cartridge distal end when the cartridge is held by but before movement of the gripper.

8. The device of claim 1, wherein the housing extends at least partly along the cartridge when in its locked position.

9. The device of claim 1, wherein the ratio housing length along cartridge axis related to total preparation height in the cartridge before expulsion thereof is less than 10.

10. The device of claim 1, wherein the piston rod in its retracted position has its second end confined within the housing.

11. The device of claim 1, wherein the piston rod has threads over at least part of its length and that the actuator for moving the piston rod includes a complementary screw-and-nut arrangement with a driven part.

12. The device of claim 11, wherein, in the screw-and-nut arrangement, the actuator is arranged to rotate the nut while means are provided for preventing the piston rod from rotating.

13. The device of claim 11, wherein, in the screw-and-nut arrangement, the actuator is arranged to rotate the piston rod while means are provided for preventing the nut from rotating.

14. The device of claim 1, wherein the actuator include a motor.

15. The device of claim 14, wherein the motor comprises at least one electric motor.

16. The device of claim 1, wherein the actuator include an energy source containing stored energy.

17. The device of claim 16, wherein the energy source comprises at least one electric source.

18. The device of claim 1, wherein the piston rod has a length less than 2 times cartridge length between a rear part of the movable wall and a cartridge interior front part.

19. The device of claim 1, the gripper is separate from the piston rod.

20. The device of claim 19, wherein the actuator includes a motor arranged for driving either the gripper or the piston rod and that a shifter is provided for shift of engagement therebetween.

21. The device of claim 1, wherein the piston rod is arranged as the gripper.

22. The device of claim 21, wherein the piston rod and the cartridge have corresponding threads and are arranged for reciprocal rotation to move the cartridge.

23. The device of claim 22, wherein the piston rod part is arranged for rotation and the cartridge part is arranged non-rotational.

24. The device of claim 22, wherein a part of the piston rod having the threads is arranged to penetrate into the cartridge interior during cartridge movement.

25. The device of claim 22, wherein the threads on the piston rod are arranged both for moving the cartridge relative the housing and for moving the piston rod relative the housing for dispensing action.

26. The device of claim 25, wherein the actuator includes a motor arranged for driving either the cartridge movement or the piston rod movement.

27. The device of claim 1, wherein the gripper comprises attachment means and moving means, the attachment means being arranged to affix the cartridge to the moving means.

28. The device of claim 27, wherein the attachment means includes a carriage for the cartridge, the carriage being attached to the gripper and having locking features for releasable connection of the cartridge thereto.

29. The device of claim 1, wherein the lock is operative to lock the cartridge against axial and rotational movements.

30. The device of claim 1, wherein the lock is operative to prevent, when engaged, removal of the cartridge and that a controller is present to impede disengagement unless the piston rod is in its retracted position.

31. The device of claim 1, further comprising at least one trigger, having a trigger release, for performing the shift and the shifter is responsive to the at least one trigger.

32. The device of claim 31, wherein the trigger for disabling the gripper and enabling the piston rod is correlated to the arrival of the gripper or cartridge to the locked position thereof.

33. The device of claim 31, wherein the trigger for enabling the gripper and disabling the piston rod is correlated to the arrival of the piston rod to its retracted position.

34. The device of claim 31, wherein the shifter includes a communicator for communication of the trigger release to disable the actuator, the communicator being mechanical.

35. The device of claim 1, wherein the shifter is are operable to enable piston rod axial movement when the cartridge is in its locked position and to enable the gripper for cartridge movement when the piston rod is in its retracted position.

36. The device of claim 1, wherein enabling and disabling respectively in the shift are performed substantially simultaneously.

37. The device of claim 1, wherein the actuator comprises a motor for both gripper and piston rod movements and that the shifter performs a shift of engagement thereof.

38. The device of claim 1, wherein the relative positions between the piston rod in its retracted position and the cartridge in its locked position being such that the piston rod extends into the cartridge beyond the initial position for the movable wall in the cartridge.

39. The device of claim 1, wherein the lock is arranged to give several locked positions along cartridge movement trajectory.

40. The device of claim 39, wherein from the piston rod, separate second gripper are arranged to move and stop the cartridge at several positions to provide the several locked positions.

41. The device of claim 1, wherein the injection device further comprises position sensing means with control means for preventing or allowing operation of the device in predetermined positions of the device.

42. The device of claim 1, wherein the injection further comprises a sensor for at least one cartridge parameter.

43. An injection device comprising a) a housing, b) a cartridge containing a preparation or precursor components for the preparation and having a front part and a rear part defining a general cartridge axis, an outlet for the preparation arranged at the front part and at least one movable wall arranged between the front part and the rear part, a displacement of which wall causes the preparation to be moved towards or expelled through the outlet, c) a piston rod, having a first end and a second end, at least partly contained within the housing and being operable to engage and displace the movable wall at its first end and d) an actuator within the housing arranged to move at least the rod, a gripper connected to the housing and arranged to hold the cartridge, or an enclosure therefore, with its front part distal and its rear part proximal to the housing, the actuator being arranged to move the gripper so as to move the cartridge, with its rear part leading, relative the housing, the actuator being able to move the movable rod between at least one retracted position and at least one extended position, and that the piston rod is arranged as a gripper whereby the cartridge moves over and along the piston rod while the piston rod is engaged with the movable wall, at least during the movement of the cartridge.

* * * * *